(12) United States Patent
Yamaki et al.

(10) Patent No.: US 10,857,323 B2
(45) Date of Patent: Dec. 8, 2020

(54) AUDIO SIGNAL GENERATION DEVICE, AUDIO SIGNAL GENERATION METHOD, AND COMPUTER-READABLE STORAGE MEDIUM

(71) Applicant: YAMAHA CORPORATION, Hamamatsu (JP)

(72) Inventors: Kiyoshi Yamaki, Iwata (JP); Morito Morishima, Fukuroi (JP); Atsushi Ishihara, Iwata (JP); Takehiko Kawahara, Hamamatsu (JP); Yuki Ueya, Iwata (JP)

(73) Assignee: YAMAHA CORPORATION, Hamamatsu (JP)

( * ) Notice: Subject to any disclaimer, the term of this patent is extended or adjusted under 35 U.S.C. 154(b) by 392 days.

(21) Appl. No.: 15/852,133

(22) Filed: Dec. 22, 2017

(65) Prior Publication Data

US 2018/0117277 A1 May 3, 2018

Related U.S. Application Data

(63) Continuation of application No. PCT/JP2016/068668, filed on Jun. 23, 2016.

(30) Foreign Application Priority Data

Jun. 29, 2015 (JP) ................. 2015-129795

(51) Int. Cl.
*A61M 21/02* (2006.01)
*G10H 1/00* (2006.01)
(Continued)

(52) U.S. Cl.
CPC .............. *A61M 21/02* (2013.01); *G10H 1/00* (2013.01); *G10H 1/38* (2013.01);
(Continued)

(58) Field of Classification Search
CPC ............ A61M 21/02; G10H 1/00; G10H 1/38
(Continued)

(56) References Cited

U.S. PATENT DOCUMENTS 5,267,942 A * 12/1993 Saperston ............. A61M 21/02
128/905
2005/0209503 A1* 9/2005 Elliott ................ A61B 5/02405
600/26
(Continued)

FOREIGN PATENT DOCUMENTS

CN  102553054 A  7/2012
JP  H04269972 A  9/1992
(Continued)

OTHER PUBLICATIONS

Office Action issued in Chinese Appin. No. 201680038730.8 dated Nov. 29, 2019. English translation provided.
(Continued)

*Primary Examiner* — Samuel G Gilbert
(74) *Attorney, Agent, or Firm* — Rossi, Kimms & McDowell LLP

(57) ABSTRACT

An audio signal generation device (20) includes: an acquirer (210) configured to acquire biological information of a human subject; an audio signal generator (245) configured to generate an audio signal based on at least one of a plurality of pieces of sound information; and a switching cycle decider (241) configured to decide a switching cycle, such that first sound information switches to second sound information at a cycle that is in accordance with the biological information, the first sound information and the second sound information being included in the plurality of sound information pieces, and the audio signal generator (245)
(Continued)

generates an audio signal based on the second sound information, at the switching cycle decided by the switching cycle decider (241).

14 Claims, 10 Drawing Sheets

(51) Int. Cl.
*G10H 1/38* (2006.01)
*A61M 21/00* (2006.01)

(52) U.S. Cl.
CPC .............. *A61M 2021/0027* (2013.01); *A61M 2021/0088* (2013.01); *A61M 2205/3303* (2013.01); *A61M 2205/3375* (2013.01); *A61M 2205/502* (2013.01); *A61M 2205/52* (2013.01); *A61M 2230/06* (2013.01); *A61M 2230/42* (2013.01); *A61M 2230/63* (2013.01); *G10H 2210/395* (2013.01); *G10H 2210/555* (2013.01); *G10H 2210/571* (2013.01); *G10H 2220/361* (2013.01); *G10H 2220/371* (2013.01)

(58) Field of Classification Search
USPC ....................................................... 600/26–28
See application file for complete search history.

(56) References Cited

U.S. PATENT DOCUMENTS

| 2007/0083079 A1* | 4/2007 | Lee | A61B 5/4806 |
| | | | 600/27 |
| 2010/0087701 A1* | 4/2010 | Berka | A61M 21/02 |
| | | | 600/27 |
| 2014/0350706 A1 | 11/2014 | Morishima | |

FOREIGN PATENT DOCUMENTS

| JP | 2004344284 A | 12/2004 |
| JP | 2011130099 A | 6/2011 |
| JP | 2014226361 A | 12/2014 |

OTHER PUBLICATIONS

International Search Report issued in Intl. Appln. No. PCT/JP2016/068668 dated Aug. 16, 2016. English translation provided.

* cited by examiner

| SOUND INFORMATION FOR BREATHING CYCLE | SOUND INFORMATION FOR HEARTBEAT CYCLE | SOUND INFORMATION FOR AMBIENT SOUND |
|---|---|---|
| BD1 | HD1 | AD1 |
| BD2 | HD2 | AD2 |
| ⋮ | ⋮ | ⋮ |
| BD10 | HD10 | AD10 |
| BD11 | HD11 | AD11 |
| BD12 | HD12 | AD12 |
| ⋮ | ⋮ | ⋮ |
| BD20 | HD20 | AD20 |
| ⋮ | ⋮ | ⋮ |

FIG. 9

| SOUND INFORMATION NAME | TYPE | TONALITY | CHORD NAME | NOTE NAME | SCALE |
|---|---|---|---|---|---|
| BD1 | CHORDAL | C MAJOR | C | - | - |
| BD2 | CHORDAL | C MAJOR | CM7 | - | - |
| BD3 | CHORDAL | C MAJOR / F MAJOR | FM7 | - | - |
| ⋮ | ⋮ | ⋮ | ⋮ | ⋮ | ⋮ |
| AD1 | - | - | - | DO | - |
| AD2 | - | - | - | DO, MI | - |
| AD3 | - | - | - | - | - |
| ⋮ | ⋮ | ⋮ | ⋮ | ⋮ | ⋮ |
| HD1 | MODAL | - | - | - | D DORIAN |
| HD2 | MODAL | - | - | - | C OKINAWAN |
| HD3 | CHORDAL | C MAJOR | Am | - | - |
| HD4 | CHORDAL | C MAJOR | F | - | - |
| HD5 | CHORDAL | C MAJOR / F MAJOR | FM7 | - | - |
| ⋮ | ⋮ | ⋮ | ⋮ | ⋮ | ⋮ |

TBLb

AUDIO SIGNAL GENERATION DEVICE, AUDIO SIGNAL GENERATION METHOD, AND COMPUTER-READABLE STORAGE MEDIUM

TECHNICAL FIELD

The present invention is directed to a technology for generating an audio signal in accordance with sound information that is related to sound generation.

BACKGROUND ART

Recently, there have been proposed technologies for enhancing sleep and imparting relaxation effects by detecting biological information of a body, such as body motion, breathing, heartbeat, and so forth, and generating a sound in accordance with the detected biological information (for example, refer to Japanese Patent Application Laid-Open Publication No. H4-269972). There have also been proposed technologies for adjusting, in accordance with a relaxation state of a human subject, at least one of a type, a volume, and a tempo of a generated sound (for example, refer to Japanese Patent Application Laid-Open Publication No. 2004-344284).

When a sound is generated to enhance sleep and the like, if a monotonous sound is generated, sleep may be impeded or disturbed in a person perceiving the sound due to boredom or annoyance.

SUMMARY OF THE INVENTION

The present invention has been made in consideration of the aforementioned circumstances, and one of the problems to be solved by the present invention is to provide a technology by which an audio signal is generated in such a manner that when sleep and the like is expected to be enhanced by a sound being generated, an impression that the sound is boring or annoying is not imparted to a human subject.

In order to solve the aforementioned problem, in one aspect, an audio signal generation device according to the present invention includes: an acquirer configured to acquire biological information of a human subject; an audio signal generator configured to generate an audio signal based on at least one of a plurality of pieces of sound information; and a switching cycle decider configured to decide a switching cycle, such that first sound information switches to second sound information at a cycle that is in accordance with the biological information, the first sound information and the second sound information being included in the plurality of sound information pieces, and the audio signal generator generates an audio signal based on the second sound information at the switching cycle decided by the switching cycle decider.

The present invention may be embodied not only in a form of an audio signal generation device, but also in a form of an operation method for the audio signal generation device (i.e., an audio signal generation method); or in a form of a program that causes a computer to execute the audio signal generation method. The program of the present invention may be stored on computer-readable storage media for installation in a computer.

BRIEF DESCRIPTION OF THE DRAWINGS

FIG. 9 is an explanatory diagram showing an example of a control table generated by a controller of an audio signal generation device according to a fourth embodiment.

MODES FOR CARRYING OUT THE INVENTION

In the following, embodiments of the present invention will be explained with reference to the drawings.

First Embodiment

Figure 1:
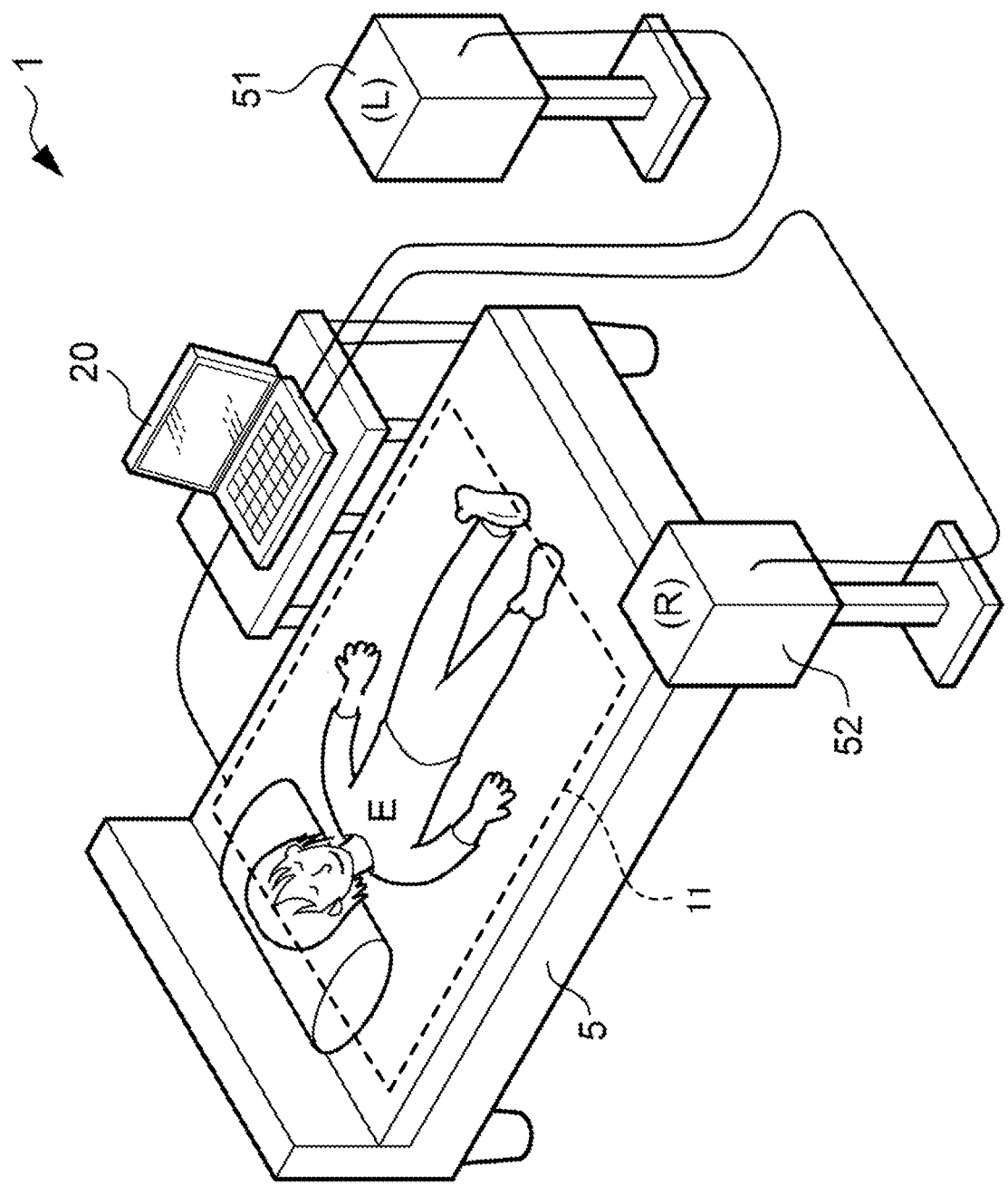
FIG. 1 is a diagram showing an overall configuration of a system including an audio signal generation device according to a first embodiment.

FIG. 1 is a diagram showing an overall configuration of a system 1 including an audio signal generation device 20 according to a first embodiment. As shown in the figure, the system 1 includes a sensor 11, the audio signal generation device 20, and speakers 51 and 52. The system 1 is provided to enhance sleep and the like by causing a sound output by the speakers 51 and 52 to be heard or perceived by a human subject E lying on his/her back on a bed 5.

The sensor 11 is constituted in a form of a sheet-like piezoelectric element, for example, and is disposed underneath a mattress on the bed 5. When the human subject E lies down on the bed 5, the sensor 11 detects biological information of the human subject E. The sensor 11 detects body motion resulting from biological activities, including breathing and a heartbeat of the human subject E, and outputs a detected signal on which components of such biological activities are superimposed. For the sake of convenience, in the figure there is shown a configuration by which the detected signal is transmitted to the audio signal generation device 20 via a wired connection; however, wireless transmission may be employed instead.

The audio signal generation device 20 is capable of obtaining a breathing cycle BRm, a heartbeat cycle HRm, and body motion of the human subject based on a detected signal (biological information) output from the sensor 11. Moreover, the audio signal generation device 20 is capable of estimating states of a mind and a body (hereinafter, "physical and mental state") of the human subject E based on the detected signal (biological information) output from the sensor 11, and information on sound (described later in more detail) that is output from the speakers 51 and 52 can be stored in association with the estimated physical and mental state. The audio signal generation device 20 is, for example, a portable terminal or a personal computer.

The speakers 51 and 52 are arranged at positions that allow the human subject E lying on his/her back to hear the stereo sound. The speaker 51 amplifies, by means of a built-in amplifier, a left (L) audio signal of stereo signals output from the audio signal generation device 20, for output as sounds. Likewise, the speaker 52 amplifies, by means of a built-in amplifier, a right (R) audio signal of stereo signals output from the audio signal generation device 20, for output as sounds. Alternatively, headphones may be employed for the human subject E to hear the sounds. Explanation of the present embodiment, however, is based on a configuration in which the speakers 51 and 52 are used.

Figure 2:
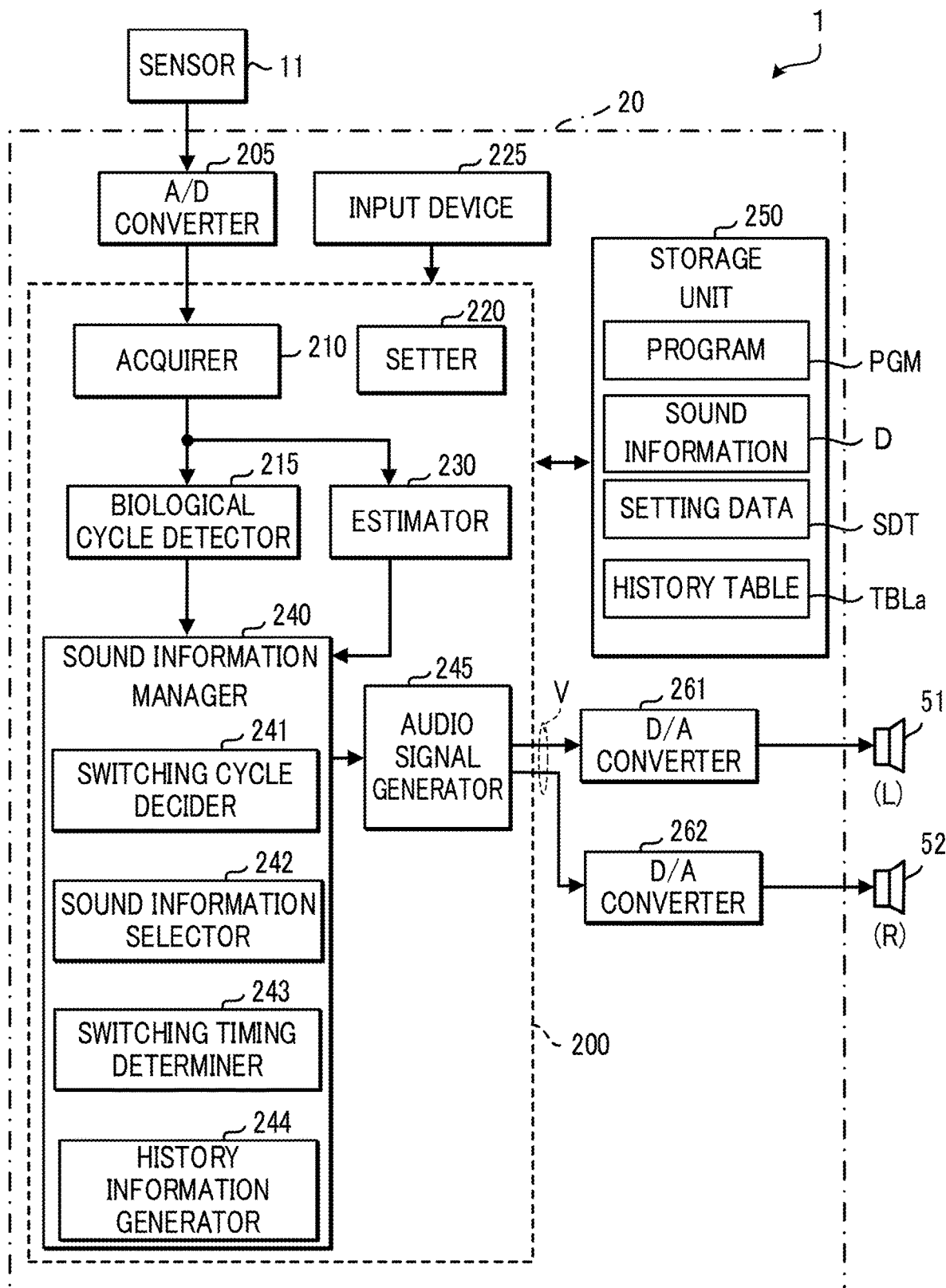
FIG. 2 is a block diagram showing a functional configuration of the audio signal generation device.

FIG. 2 is a block diagram mainly showing a configuration of functional blocks in the audio signal generation device 20, in the system 1. As shown in the figure, the audio signal generation device 20 includes an A/D converter 205, a controller 200, a storage unit 250, an input device 225, and D/A converters 261 and 262. The storage unit 250 is a non-transitory storage medium, for example, and may be an optical storage medium, such as a CD-ROM (optical disc), or well-known storage media, such as a magnetic storage medium and a semiconductor storage medium. As used in the present description the term "non-transitory" storage medium includes all types of computer-readable storage media, including volatile storage media, with the only exception being that of transitory, propagating signals. In the storage unit 250 a program PGM is stored to be executed by the controller 200 and various data to be used by the controller 200. For example, the storage 250 stores a plurality of sound information pieces (sound contents) D, and a history table TBLa in which information on sound output by the speakers 51 and 52 is stored in association with an estimated physical and mental state of the human subject E. The program PGM may be provided, being delivered via a communication network (not shown) for installation in the storage unit 250.

The input device 225 is a touch panel, for example, and acts as an input/output device having a display unit (e.g., a liquid-crystal display panel) and an input unit integrated therein, with the display unit displaying various images under control of the controller 200, and the input unit accepting instructions input for the audio signal generation device 20 by a user (e.g., the human subject). A configuration may be adopted in which the input device 225 is configured as a device having a plurality of operation elements provided separately from a display unit.

The controller 200 consists of a processing device (such as a CPU), for example, and by executing the program PGM stored in the storage unit 250, functions as an acquirer 210, a biological cycle detector 215, a sound information manager 240, a setter 220, an estimator 230, and an audio signal generator 245. The entirety or a part of these functions can be realized by dedicated electronic circuitry. For example, the audio signal generator 245 may be configured as a large-scale integration (LSI). The plurality of sound information pieces D stored in the storage unit 250 may be any data in so far as the audio signal generator 245 can generate audio signals V ($V_L$ and $V_R$) based on the sound information pieces D. The sound information pieces D may be, for example, performance data representing performance information such as notes and pitch (pace), parameter data representing parameters and the like that are used to control the audio signal generator 245, or waveform data.

Figures 3, 4:
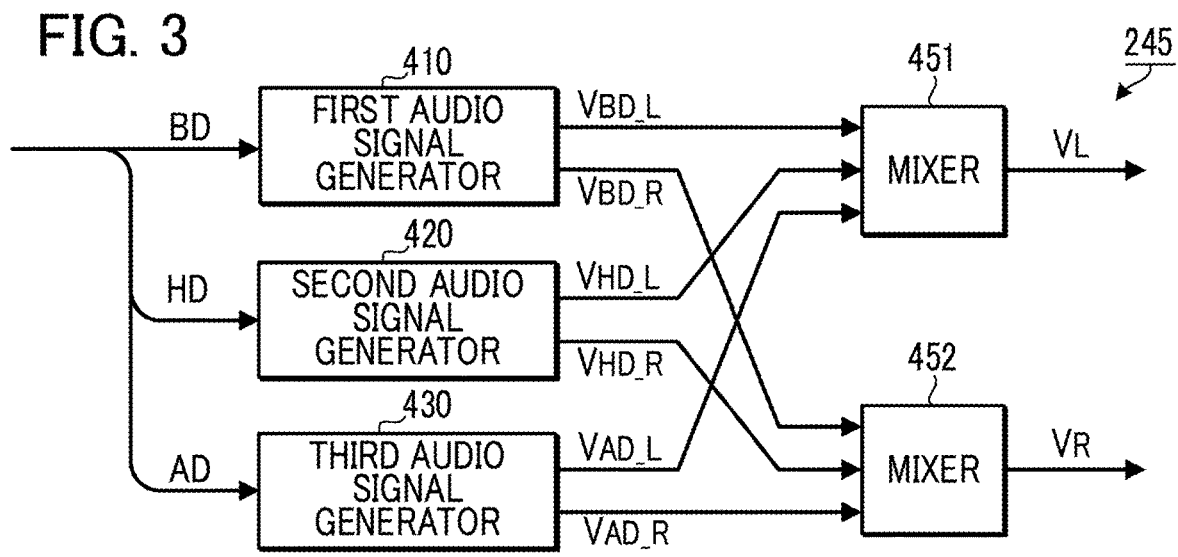
FIG. 3 is a block diagram showing an example configuration of a sound source of the audio signal generation device.
FIG. 4 is an explanatory diagram showing details of a content stored in a storage unit of the audio signal generation device.

FIG. 4 shows examples of the plurality of sound information pieces D stored in the storage unit 250. As shown in the figure, in the storage unit 250 there is stored each of sound information BD (BD1, BD2, . . . ) for a breathing cycle, sound information HD (HD1, HD2, . . . ) for a heartbeat cycle, and sound information AD (AD1, AD2, . . . ) for an ambient sound. As will be described in more detail later, the sound information BD for a breathing cycle is used for generating an audio signal at a cycle that is in accordance with the breathing cycle BRm; the sound information HD for a heartbeat cycle is used for generating an audio signal at a cycle that is in accordance with the heartbeat cycle HRm; and the sound information AD for an ambient sound is used for generating an audio signal at a cycle that is independent of both the breathing cycle BRm and the heartbeat cycle HRm.

The A/D converter 205 converts the signals detected by the sensor 11 into digital signals. The acquirer 210 temporarily stores the converted digital signals in, for example, the storage unit 250. The biological cycle detector 215 detects a biological cycle of the human subject E, based on the biological information stored in the storage unit 250. In the present embodiment, the biological cycle detector 215 detects the heartbeat cycle HRm and the breathing cycle BRm as biological cycles, and supplies the same to the sound information manager 240. Specifically, the biological cycle detector 215 extracts, from the detected signal acquired by the acquirer 210, signal components of a frequency band that correspond to the breathing component, and detects the respiration cycle BRm of the human subject E based on the extracted components. From the detected signal, the biological cycle detector 215 also extracts signal components of a frequency band corresponding to the heartbeat component, for detection of the heartbeat cycle HRm of the human subject E based on the extracted components. The estimator 230 estimates the physical and mental state of the human subject E based on the biological information stored in the storage unit 250, and supplies to the sound information manager 240 information indicative of the estimated physical and mental state.

The setter 220 is used to carry out a variety of settings. The audio signal generation device 20 is capable of playing a large number of musical sounds so that the human subject E does not become bored. The setter 220 sets a tone color of the musical sound in accordance with an input operation performed by the human subject E on the input device 225, and temporarily stores in the storage unit 250 details of the setting as setting data SDT.

In the present embodiment, the estimator 230 estimates from detection results of the sensor 11 the physical and mental state (sleep stages) of the human subject E over a period extending from a time point at which the human subject E enters a calm state and then falls asleep, until a time point at which the human subject E awakens. The estimator 230 estimates whether the human subject E is in an "awake" state, a "light sleep" state, a "deep sleep" state, or a "REM sleep" state. Each of a "light sleep" state and a "deep sleep" state may be a "Non-REM sleep" state.

As a state of a human transitions from wakefulness to deep sleep state, a breathing cycle BRm and a heartbeat cycle HRm of the human tend to become longer. Also, fluctuations in these cycles tend to become smaller.

In addition, body motion tends to decrease as sleep deepens. Taking the foregoing into consideration, the estimator 230, based on the signals detected by the sensor 11, obtains a value from changes in the breathing cycle BRm and the heartbeat cycle HRm with a number of body movements per unit time, and compares the obtained value with a plurality of thresholds, thereby to estimate a physical and mental state.

The sound information manager 240 is a functional element that executes a variety of functions related to processing of the sound information D. Specifically, as shown in FIG. 2, the sound information manager 240 includes a switching cycle decider 241, a sound information selector 242, a switching timing determiner 243, and a history information generator 244. The sound information selector 242 decides (selects), based on the setting data SDT stored in the storage unit 250, which one of the plurality of sound information pieces D stored in the storage unit 250 is to be read and played, and supplies to the audio signal generator 245 designation data that designates the selected sound information D. Specifically, the sound information selector 242 selects at least one of the sound information BD for a breathing cycle, the sound information HD for a heartbeat cycle, or the sound information AD for an ambient sound, based on the setting data SDT stored in the storage unit 250. The history information generator 244 stores the physical and mental state estimated by the estimator 230 together with an identifier of the selected sound information D in association with a processing time of the selected sound information D (for example, a time at which an audio signal based on the selected sound information D was generated), in the history table TBLa stored in the storage unit 250.

The switching cycle decider 241 decides a cycle at which first sound information D is switched to second sound information D, for each of the sound information BD for a breathing cycle and the sound information HD for a heartbeat cycle. The switching cycle decider 241 decides a cycle such that the first sound information D switches to the second sound information D at a cycle (switching cycle) that is in accordance with the biological cycle detected by the biological cycle detector 215. Specifically, the switching cycle decider 241 decides a cycle that is in accordance with a cycle of the breathing cycle BRm detected by the biological cycle detector 215 (e.g., a cycle obtained by multiplying the breathing cycle BRm by a predetermined number), as a switching cycle of the sound information BD for a breathing cycle. Likewise, the switching cycle decider 241 decides a cycle that is in accordance with a cycle of the heartbeat cycle HRm (e.g., a cycle obtained by multiplying the heartbeat cycle HRm by a predetermined number), as a switching cycle of the sound information HD for a heartbeat cycle.

The switching timing determiner 243 determines whether a current time corresponds to a switching timing according to the switching cycle decided by the switching cycle decider 241 for either the sound information BD for a breathing cycle or the sound information HD for a heartbeat cycle. Furthermore, the switching timing determiner 243 determines whether a current time corresponds to a switching timing according to a cycle that is freely set as a switching cycle for an ambient sound (or a cycle that is in accordance with the switching cycle of the sound information BD for a breathing cycle, or a cycle that is in accordance with the switching cycle of the sound information HD for a heartbeat cycle).

Here, the "first sound information D" is sound information D prior to the switching, and the "second sound information D" is sound information D to which the first sound information D is switched. In other words, "first sound information D" is sound information D based on which the most recently generated audio signal V was generated; and "second sound information D" is sound information D based on which an audio signal V is to be generated following the generation of the audio signal V for the "first sound information D", the second sound information D having been selected as a result of sound information pieces D sequentially being selected by the sound information selector 242. That is, the "first sound information D" and the "second sound information D" are freely-selected two sound information pieces D, based on which audio signals V are generated in a chronologically consecutive order.

The audio signal generator 245 acquires sound information D corresponding to designation data supplied from the sound information selector 242, with the sound information being acquired from the storage unit 250 and at a switching cycle decided by the switching cycle decider 241. Then, the audio signal generator 245 generates an audio signal V based on the acquired sound information D and plays a musical sound. FIG. 3 shows a detailed configuration of the audio signal generator 245. The audio signal generator 245 includes first to third audio signal generators 410 to 430, and mixers 451 and 452.

The first audio signal generator 410 generates audio signals $V_{BD}$ ($V_{BD\_L}$ and $V_{BD\_R}$) that are based on the audio signal BD for a breathing cycle, at a cycle linked to the breathing cycle BRm. The second audio signal generator 420 generates audio signals $V_{HD}$ ($V_{HD\_L}$ and $V_{HD\_R}$) that are based on the sound information HD for a heartbeat cycle, at a cycle linked to the heartbeat cycle HRm. The third sound signal generator 430 generates audio signals $V_{AD}$ ($V_{AD\_L}$ and $V_{AD\_R}$) that are based on the sound information AD for an ambient sound, at a cycle not linked to either the breathing cycle BRm or the heartbeat cycle HRm.

Specifically, in the present embodiment, each of the first to third audio signal generators 410 to 430 acquires from the storage unit 250 the second sound information D (BD, HD, or AD) that has been selected by the sound information selector 242 individually for each of the sound information BD for a breathing cycle, the sound information HD for a heartbeat cycle, and the sound information AD for an ambient sound. The first to third audio signal generators 410 to 430 acquire these second sound information pieces D at switching cycles that have been decided by the switching cycle decider 241 individually for each of the first to third audio signal generators 410 to 430. Each of the first to third audio signal generators 410 to 430 generates the audio signals V ($V_{BD}$, $V_{HD}$, or $V_{AD}$) based on the corresponding second sound information D acquired, and outputs the same in a digital, stereo (two-channel) format as audio signals $V_{BD}$ ($V_{BD\_L}$ and $V_{BD\_R}$), $V_{HD}$ ($V_{HD\_L}$ and $V_{HD\_R}$), or V ($V_{AD\_L}$ and $V_{AD\_R}$).

The mixer 451 mixes (synthesizes) the left (L) audio signals $V_{BD\_L}$, $V_{HD\_L}$, and $V_{AD\_L}$ output from the first to third audio signal generators 410 to 430, to generate an audio signal $V_L$ for output. Likewise, the mixer 452 mixes the right (R) audio signals $V_{BA\_R}$, $V_{HD\_R}$, and $V_{AD\_R}$ output from the audio signal generators 410 to 430, to generate an audio signal $V_R$ for output.

The D/A converter 261 converts the left (L) audio signal $V_L$ obtained through mixing by the mixer 451 into analog and outputs the same. Likewise, the D/A converter 262 converts the right (R) audio signal $V_R$ obtained through mixing by the mixer 452 into analog and outputs the same.

In the present embodiment, the switching cycle decider 241 decides a switching cycle such that the first sound information D is switched to the second sound information D at a cycle that is in accordance with the biological information of the human subject E. Each of the first to third audio signal generators 410 to 430 generates an audio signal based on the second sound information D (i.e., switches from the first sound information D to the second sound information D), at the switching cycle decided by the switching cycle decider 241. This process is defined as "generating sound information D (the second sound information D that is the sound information after the switching) at a cycle linked to a biological cycle" or as "switching the first sound information D to the second sound information D at a cycle linked to a biological cycle".

A playback period of sound based on the sound information BD for a breathing cycle stored in the storage unit 250 is 10 seconds. In general, a breathing cycle BRm of a human in a calm state is approximately 5 to 8 seconds. The playback period is set to 10 seconds because in switching from a sound information piece BD for a breathing cycle to a new sound information piece BD at a cycle that is in accordance with the breathing cycle BRm, it is preferable that the sound corresponding to one sound information piece BD is played over the entire period of the breathing cycle BRm. The same is applicable to the sound information HD for a heartbeat cycle. That is, a playback period of the sound information HD for a heartbeat cycle is set to have a greater time length than an average heartbeat cycle HRm of a human.

Figure 5:
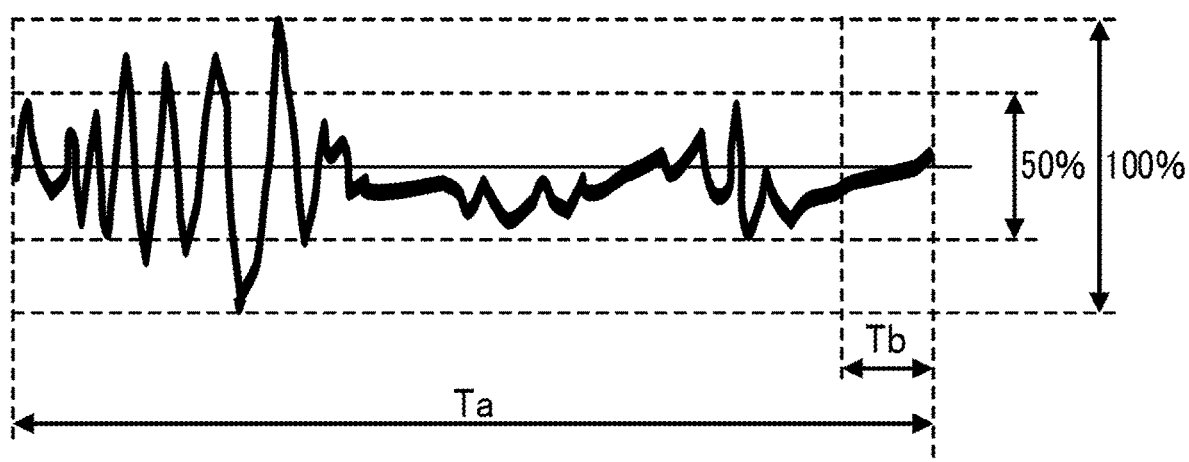
FIG. 5 is a waveform diagram showing an example of waveform data.

FIG. 5 shows an example of a waveform of the audio signal V generated by the audio signal generator 245 based on the sound information BD for a breathing cycle. As shown in the figure, a length of an entire playback period Ta of the waveform corresponding to the sound information BD for a breathing cycle is, for example, 10 seconds. When a difference (in the axis of amplitude) between a maximum value of an upper peak of the waveform and a minimum value of a lower peak of the waveform is taken as 100%, a difference between an upper peak and a lower peak of the waveform in the latter half of the playback period is set to be 50% or less. In particular, when the entire playback period Ta is taken as 100%, in a period Tb, which consists of the final 10% of the playback period Ta, it is preferable for a difference between an upper peak and a lower peak of the waveform to be set at 50% or less. As described above, the waveform is attenuated in the latter half of the playback period, and thus a sound information piece BD for a breathing cycle is switched to a new sound information piece BD at a cycle that is in accordance with the breathing cycle BRm of the human subject. As with switching the sound information pieces BD for a breathing cycle, a sound information piece HD for a heartbeat cycle is switched to a new sound information piece HD at a cycle that is in accordance with the heartbeat cycle HRm. Accordingly, as with switching the sound information BD for a breathing cycle, a waveform of the sound information HD for a heartbeat cycle may be attenuated in the latter half thereof.

Further description with reference to FIG. 4 will now be given. A plurality of sound information pieces BD for a breathing cycle are managed by being grouped into a plurality of groups. In the present example, the sound information pieces BD1, BD2 . . . BD10 for a breathing cycle are grouped in a first group, and the sound information pieces BD11, BD12 . . . BD20 for a breathing cycle are grouped in a second group. The first group may include, for example, the sound information pieces BD of a piano sound, while the second group may include, for example, the sound information pieces BD of a harp sound. The sound information pieces may also be grouped according to other musical instruments, such as a drum or a guitar. The sound information pieces BD for a breathing cycle that belong to each group differ from one another.

A length of a playback period of each of a plurality of sound information pieces HD for a heartbeat cycle is 1.2 seconds. As with management of the sound information pieces BD for a breathing cycle, the plurality of sound information pieces HD for a heartbeat cycle are managed by being grouped into a plurality of groups. In the present example, sound information pieces HD1, HD2 . . . HD10 for a heartbeat cycle are grouped in a first group, and sound information pieces HD11, HD12 . . . HD20 for a heartbeat cycle are grouped in a second group. The first group may include, for example, the sound information pieces HD of a bell sound, while the second group may include, for example, the sound information pieces HD of a wind chime sound. The sound information pieces may also be grouped according to other musical instruments, such as a drum or a guitar. The sound information pieces HD for a heartbeat cycle belonging to each group differ from one another.

Next, a length of a playback period of each of a plurality of sound information pieces AD for an ambient sound is 100 seconds. As with management of the sound information pieces BD for a breathing cycle, the plurality of sound information pieces AD for an ambient sound are managed by being grouped into a plurality of groups. In the present example, sound information pieces AD1, AD2 . . . AD10 for an ambient sound are grouped in a first group, and sound information pieces AD11, AD12 . . . AD20 for an ambient sound are grouped in a second group. The first group consists of the plurality of sound information pieces AD, which, for example, may replicate a sound of waves. The second group consists of the sound information pieces AD, which, for example, may replicate a murmuring sound of a stream. These groups may also be distinguished from one another by replicating respectively a sound of wind or a sound of a crowd.

Figure 6:
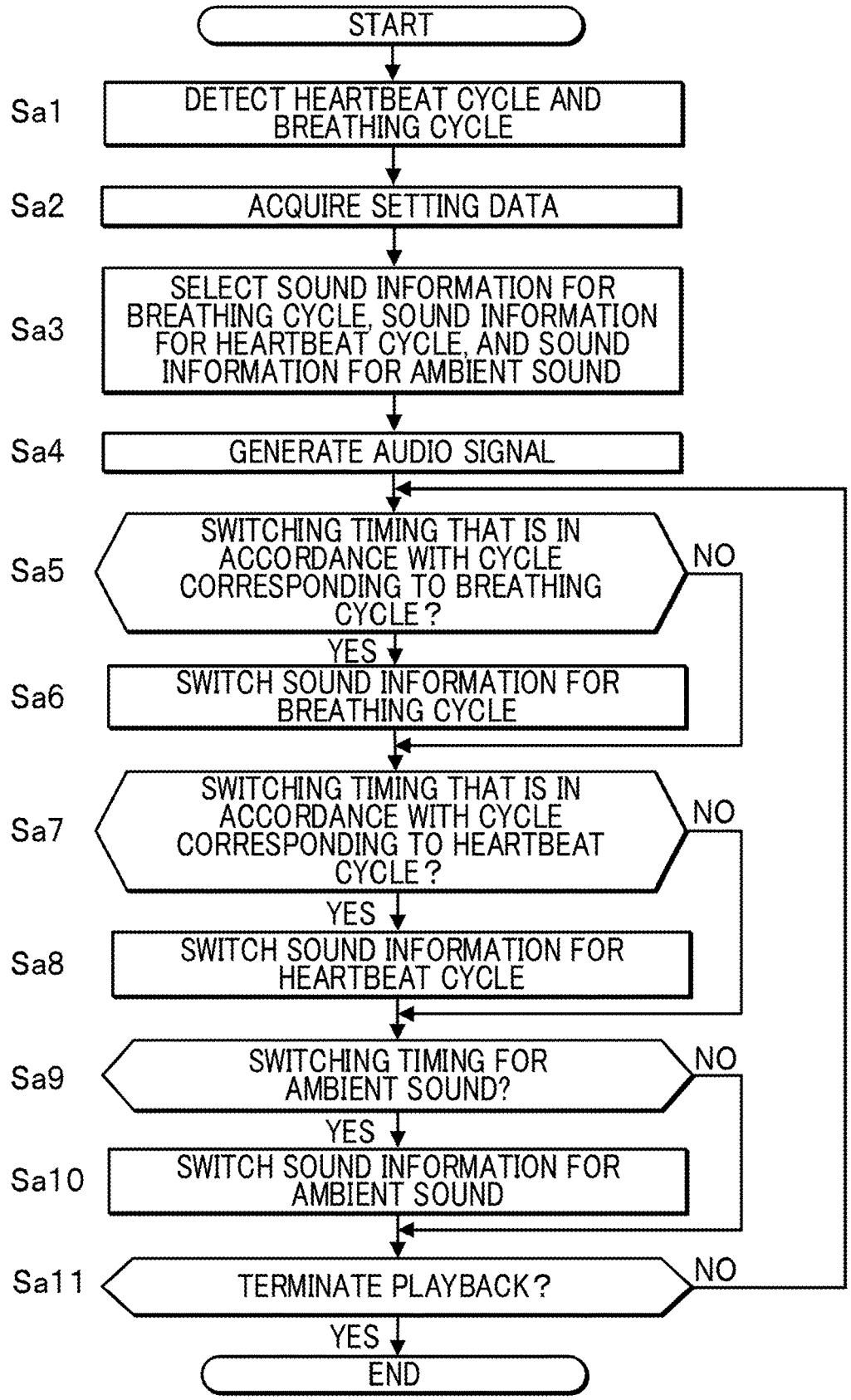
FIG. 6 is a flowchart showing a flow of an operation of the audio signal generation device.

An operation of the system 1 will now be explained. FIG. 6 is a flowchart showing an example of a flow of an operation of the audio signal generation device 20. First, the biological cycle detector 215 detects the heartbeat cycle HRm and the breathing cycle BRm of the human subject E, based on the detected signal indicative of the biological information of the human subject E acquired by the acquirer 210 (Sa1). The frequency band including breathing components superimposed on the detected signal is in a range of from about 0.1 Hz to 0.25 Hz, and the frequency band including heartbeat components superimposed on the detected signal is a range of from about 0.9 Hz to 1.2 Hz. From the detected signal at a frequency band in which breathing components are included the biological cycle detector 215 extracts signal components, and based on the extracted signal components detects the breathing cycle BRm of the human subject E. From the detected signal at a frequency band in which heartbeat components are included the biological cycle detector 215 extracts signal components, and based on the extracted signal components detects the heartbeat cycle HRm of the human subject E. The biological cycle detector 215 constantly detects the heartbeat cycle HRm and the breathing cycle BRm of the human subject E while the processes described below are being carried out.

The sound information selector 242 acquires from the storage unit 250 setting data SDT set by the setter 220 (Sa2), and based on the setting data SDT, decides a group from which to select sound information D for each of the sound information BD for a breathing cycle, the sound information HD for a heartbeat cycle, and the sound information AD for an ambient sound. The setting data SDT includes at least information that designates one of the sound information BD for a breathing cycle, the sound information HD for a heartbeat cycle, and the sound information AD for an ambient sound. In addition, the setting data SDT may also include information indicating a favorite tone color selected by the human subject E, together with information indicating a kind of musical instrument, and other relevant information.

In the present operation example, it is assumed that the setting data SDT designates all of the sound information BD for a breathing cycle, the sound information HD for a heartbeat cycle, and the sound information AD for an ambient sound. However, a configuration may instead be employed in which the setting data SDT designates at least one of these. For example, a configuration may be employed in which the setting data SDT designates the sound information BD for a breathing cycle and the sound information AD for an ambient sound, but not the sound information HD for a heartbeat cycle. In this case, for each of the sound information BD for a breathing cycle and the sound information AD for an ambient sound, the sound information selector 242 decides a group from which to select the sound information. In a case in which the setting data SDT designates all of the sound information BD for a breathing cycle, the sound information HD for a heartbeat cycle, and the sound information AD for an ambient sound, the sound information BD for a breathing cycle, the sound information HD for a heartbeat cycle, and the sound information AD for an ambient sound are mixed and are output from the audio signal generator 245 as an audio signal V. In a case in which the setting data SDT only designates the sound information BD for a breathing cycle and the sound information AD for an ambient sound, then the sound information BD for a breathing cycle and the sound information AD for an ambient sound are mixed and are output from the audio signal generator 245 as an audio signal V.

The sound information selector 242 selects one of the sound information pieces D that are included in the group that has been decided as the group from which to select the sound information D according to a prescribed rule, which in this example is a random selection rule. When the sound information D is selected at random, the same sound information BD for a breathing cycle may be selected continuously and repeatedly. Thus, a case may arise where the first sound information D and the second sound information D before and after the switching are identical. In contrast though, when the first sound information D and the second sound information D differ from each other, variations increase in sounds played for the human subject E.

Next, the sound information selector 242 selects from each of the decided groups the sound information BD for a breathing cycle, the sound information HD for a heartbeat cycle, and the sound information AD for an ambient sound, in accordance with a prescribed rule (Sa3). The rule in the present example corresponds to random selection. It is of note that a concept of randomness in the present description includes so-called pseudo randomness. For example, pseudorandom signals generated by a maximal length sequence generator may be used in selecting the sound information BD for a breathing cycle, the sound information HD for a heartbeat cycle, and the sound information AD for an ambient sound.

Next, the audio signal generator 245 generates an audio signal V, using randomly selected sound information BD for a breathing cycle, sound information HD for a heartbeat cycle, and sound information AD for an ambient sound (Sa4).

Next, the switching timing determiner 243 determines whether a current time corresponds to a switching timing that is in accordance with a cycle according to the breathing cycle BRm of the human subject E (Sa5). Specifically, the switching timing determiner 243 determines whether, at a current time, a period corresponding to a switching cycle for a breathing cycle has passed since a time point at which the sound information BD for a breathing cycle most recently acquired by the audio signal generator 245 from the storage unit 250 started to play. (The time point at which the sound information BD started to play may, for example, be a time point at which the sound information BD was acquired.) Here, the "switching cycle for a breathing cycle" is a cycle that is in accordance with the breathing cycle BRm, and need not necessarily coincide with the detected breathing cycle BRm. It is sufficient if a particular relationship exists between the switching cycle for a breathing cycle and the detected breathing cycle BRm. For example, breathing cycles BRm detected by the biological cycle detector 215 within a prescribed period may be averaged, and the obtained average value may be multiplied by K (K is a freely-selected value satisfying $1 \leq K \leq 1.1$). In the present example, the average value is multiplied by 1.05 to set a switching cycle of the sound information BD for a breathing cycle. In this case, given that the average value of the breathing cycles BRm of the human subject E is 5 seconds, the switching cycle is set at 5.25 seconds. As stated, a breathing cycle BRm tends to become longer as a person becomes more relaxed. Accordingly, it is expected that by setting the switching cycle to be slightly longer than the measured breathing cycle BRm, a person will be caused to relax and fall asleep quickly. The switching cycle for a breathing cycle is decided by the switching cycle decider 241 based on the breathing cycle BRm detected by the biological cycle detector 215. It is preferred that the switching cycle for a breathing cycle is decided for every prescribed period described above (the unit period used to calculate the average value).

When a determination condition in step Sa5 is affirmed, the switching timing determiner 243 supplies to the audio signal generator 245 a timing signal instructing generation of a new sound information piece BD for a breathing cycle (second sound information BD). When the timing signal is supplied, the first audio signal generator 410 of the audio signal generator 245 acquires from the storage unit 250 the sound information piece BD for a breathing cycle selected by the sound information selector 242, as the second sound information BD. Then, the first audio signal generator 410 generates the audio signal $V_{BA}$ based on the acquired second sound information BD (Sa6). The sound information selector 242 selects a sound information piece BD each time a generation timing based on the sound information BD for a breathing cycle (a switching cycle for a breathing cycle) arrives, and the selected sound information piece BD is supplied to the audio signal generator 245 together with the timing signal.

When a determination condition in step Sa5 is denied, or when a process in step Sa6 is completed, the switching timing determiner 243 determines whether a current time corresponds to a switching timing of a cycle according to the heartbeat cycle HRm of the human subject E (Sa7). In step Sa7, the switching cycle decider 241 first decides a switching cycle for a heartbeat cycle based on the heartbeat cycle HRm detected by the biological cycle detector 215. Here, the "switching cycle for a heartbeat cycle" is a cycle in accordance with the heartbeat cycle HRm, and need not necessarily coincide with the detected heartbeat cycle HRm.

It is sufficient if a particular relationship exists between the switching cycle for a heartbeat cycle and the detected heartbeat cycle BRm. For example, the detected heartbeat cycles HRm within a prescribed period may be averaged, and the obtained average value may be multiplied by L (L is a freely-selected value satisfying 1≤L≤1.1). In the present example, the average value multiplied by 1.02 is set to be a switching cycle of the sound information HD for a heartbeat cycle. In this case, given that the average value of the heartbeat cycles HRm of the human subject E is 1 second, the switching cycle is 1.02 seconds. Again, as stated, the heartbeat cycle HRm tends to become longer as a person becomes more relaxed. It is thus expected that by setting the switching cycle to be longer than the actual heartbeat cycle HRm, the human subject E can be caused to relax and fall asleep quickly. The switching cycle for a heartbeat cycle is decided by the switching cycle decider 241 based on the heartbeat cycle HRm detected by the biological cycle detector 215. It is preferable that the switching cycle for a heartbeat cycle is decided for every prescribed period (the unit period used to calculate the average value of heartbeat cycles HRm), as in the case of the switching cycle for a breathing cycle.

When a determination condition in step Sa7 is affirmed, the switching timing determiner 243 supplies to the audio signal generator 245 a timing signal instructing generation of a new sound information piece HD for a heartbeat cycle (second sound information HD). When the timing signal is supplied, the second audio signal generator 420 of the audio signal generator 245 acquires from the storage unit 250 the sound information HD for a breathing cycle selected by the sound information selector 242, as the second sound information HD. Then, the second audio signal generator 420 generates the audio signal $V_{HD}$ based on the acquired second sound information HD (Sa8). The sound information selector 242 selects a sound information piece HD every time a generation timing based on a new sound information piece HD for a heartbeat cycle (a switching cycle for a heartbeat cycle) arrives, and the selected second sound information piece HD is supplied to the audio signal generator 245 together with the timing signal.

When a determination condition in step Sa7 is denied, or when a process in step Sa8 is completed, the switching timing determiner 243 determines whether a current time corresponds to a switching timing for an ambient sound (Sa9). The switching timing for an ambient sound may be freely set. For example, the switching timing for an ambient sound may correspond to 100 seconds. Alternatively, a timing at which playback of a single piece of sound information AD for an ambient sound ends may be set as the switching timing. Further, the switching timing for an ambient sound may be set to correspond to a cycle obtained by multiplying a cycle that is in accordance with either the breathing cycle BRm or the heartbeat cycle HRm by Q, where Q is a natural number of 2 or more. For example, when Q=10, the sound information AD for an ambient sound is switched at a cycle that is ten times the rate of the switching cycle of the sound information BD for a breathing cycle. In the case of Q=10, the switching timing for the sound information BD for a breathing cycle and the switching timing for the sound information AD for an ambient sound may or may not coincide with each other. In a case in which the switching cycle for an ambient sound is set so as to be linked to a cycle that is in accordance with either the breathing cycle BRm or the heartbeat cycle HRm, the switching cycle for an ambient sound is decided by the switching cycle decider 241 based either on the breathing cycle BRm or on the heartbeat cycle HRm detected by the biological cycle detector 215.

When a determination condition in step Sa9 is affirmed, the switching timing determiner 243 supplies to the audio signal generator 245 a timing signal instructing generation of a new sound information piece AD for an ambient sound (second sound information AD). When the timing signal is supplied, the third audio signal generator 430 of the audio signal generator 245 acquires from the storage unit 250 the sound information AD for an ambient sound selected by the sound information selector 242, as the second sound information AD. Then, the third audio signal generator 430 generates the audio signal $V_{AD}$ based on the acquired second sound information AD (Sa10). The sound information selector 242 selects a sound information piece AD each time a generation timing based on a new sound information piece AD for an ambient sound (a switching cycle for an ambient sound) arrives, and the selected sound information piece AD is supplied to the audio signal generator 245 together with the timing signal. The sound information selector 242 selects at random the sound information AD for an ambient sound, in substantially the same way as in selecting the sound information BD and the sound information HD. Thus, variations in sounds caused to be heard by the human subject E can be increased.

When a determination condition in step Sa9 is denied, or when a process in step Sa10 is completed, the controller 200 determines whether or not to terminate the playback of the sound information D (Sa11). The controller 200 terminates an audio signal generation process of the present embodiment in a case in which an input instruction instructing termination of playback is input via the input device 225, or in a case in which at a current time, a time point corresponding to an end of a playback period set in advance has already passed (Sa11: YES). When a determination condition in step Sa11 is not satisfied, the controller 200 returns the process to step Sa5 and repeats the processes in steps Sa5 to Sa10. The biological cycle detector 215 constantly detects the heartbeat cycle HRm and the breathing cycle BRm. Thus, when there are changes in the heartbeat cycle HRm and the breathing cycle BRm, then by following these changes, the switching cycle for switching the sound information BD for a breathing cycle and the switching cycle for switching the sound information HD for a heartbeat cycle also change. In a particular case (i.e., a case in which the switching cycle is set to be Q times the heartbeat cycle HRm or the breathing cycle BRm), the switching cycle of the sound information AD for an ambient sound also changes.

In the first embodiment, as described above, an audio signal linked to the breathing cycle BRm and the heartbeat cycle HRm can be played without controlling a volume, or a pitch etc., of a sound. Moreover, sounds with a variety of tone colors can be played based on a limited amount of sound information. In particular, the audio signal generation device 20 of the present embodiment selects sound information pieces D at random instead of selecting the same sound information D repeatedly, and therefore, an unnatural feeling, such as the sound becoming boring or annoying to the ear, can be eliminated. In addition, it is well known that sounds having a relaxing or healing effect tend to induce a waves in the brain. Such sounds are those that have natural fluctuation components. Thus, by selecting at random sound information pieces D related to such sounds, playback of sounds of a plurality of sound information pieces D are caused to fluctuate over the plurality of sound information pieces D. Moreover, by a setting operation performed by the human subject E on the setter 220, it is possible to set each of the sound information BD for a breathing cycle, the sound information HD for a heartbeat cycle, and the sound information AD for an ambient sound selected or non-selected, namely, selecting whether to play these sound information pieces.

Second Embodiment

In the case of the audio signal generation device 20 according to the first embodiment described in the foregoing, the switching cycle for switching the sound information BD for a breathing cycle and the switching cycle for switching the sound information HD for a heartbeat cycle are set independently of each other. In contrast, an audio signal generation device 20 according to a second embodiment differs from that of the first embodiment in that the audio signal generation device 20 according to the second embodiment sets a switching cycle for switching sound information BD for a breathing cycle so as to be linked to a heartbeat cycle HRm of a human subject. Regarding other features, the audio signal generation device 20 according to the second embodiment is configured in substantially the same way as the audio signal generation device 20 according to the first embodiment.

Figure 7:
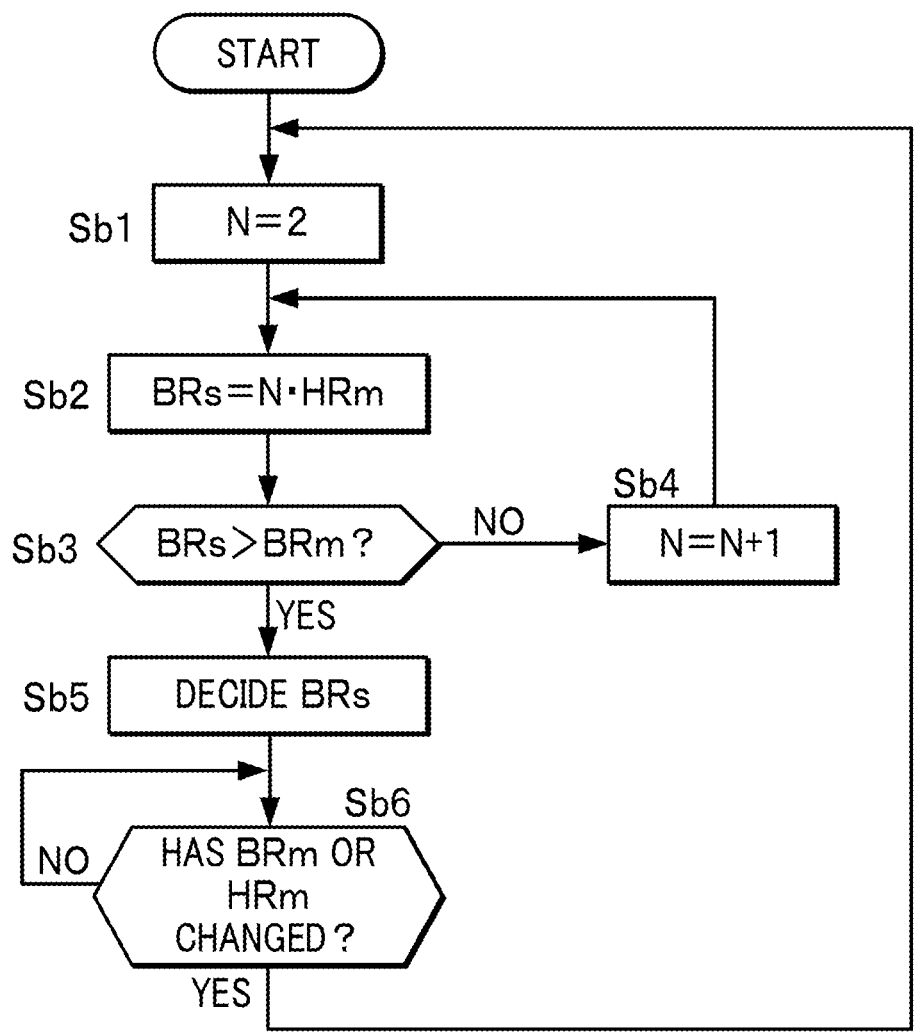
FIG. 7 is a flowchart showing a flow of an operation of a controller according to a second embodiment.

FIG. 7 is a flowchart showing a flow of an operation for deciding a switching cycle of sound information BD for a breathing cycle.

First, a switching cycle decider 241 sets an initial value of a coefficient N to "2" (Sb1). Next, the switching cycle decider 241 calculates a switching cycle BRs in accordance with Expression 1 below (Sb2).

$$BRs = N \cdot HRm \qquad \text{Expression 1}$$

Here, HRm is a heartbeat cycle measured by the biological cycle detector 215.

Next, the sound information manager 240 compares the calculated switching cycle BRs with the breathing cycle BRm measured by the biological cycle detector 215, and determines whether the switching cycle BRs exceeds the breathing cycle BRm (Sb3). When the switching cycle BRs is equal to or less than the breathing cycle BRm, the switching cycle decider 241 advances the process to Sb4 and increments the coefficient N by "1" (Sb4).

Then the switching cycle decider 241 repeats the processes in steps Sb2 to Sb4 until the switching cycle BRs extends beyond the breathing cycle BRm. When the switching cycle BRs extends beyond the breathing cycle BRm, the switching cycle BRs is decided as a cycle at which the sound information pieces BD for a breathing cycle are switched (Sb5). For example, it is provided that the measured breathing cycle BRm is 5.3 seconds and the measured heartbeat cycle HRm is 1 second. Here, in the case of N=5, the switching cycle BRs is shorter than the measured breathing cycle BRm, and thus the switching cycle BRs is not decided as a cycle for switching the sound information BD. In the case in which N becomes 6, however, the switching cycle BRs (6 seconds) extends beyond the measured breathing cycle BRm (5.3 seconds), and thus the switching cycle BRs is set at 6 seconds. It is of note that the breathing cycle BRm is equal to or more than twice the heartbeat cycle HRm, and so N will be a natural number of 2 or more.

Next, the switching cycle decider 241 determines whether either one of the measured breathing cycle BRm and the measured heartbeat cycle HRm has changed (Sb6). The sound information manager 240 repeats the determination until a determination condition is satisfied. When the determination condition is satisfied, the switching cycle decider 241 returns the process to step Sb1.

In the manner described above, the audio signal generation device 20 according to the second embodiment switches a sound information piece BD for a breathing cycle to a new sound information piece BD, so as to be linked to the measured heartbeat cycle HRm. In the present example, the switching cycle of the sound information BD for a breathing cycle is decided such that the switching cycle is a natural-number multiple of the measured heartbeat cycle HRm. However, the switching cycle of the sound information BD for a breathing cycle may be decided such that the switching cycle is a natural-number multiple of the switching cycle of the sound information HD for a heartbeat cycle.

In this case, the switching cycle HRs of the sound information pieces HD for a heartbeat cycle may be used in place of the measured heartbeat cycle HRm of the above description. The switching cycle BRs for a breathing cycle is a natural-number multiple of the switching cycle HRs for a heartbeat cycle, and therefore, the switching cycle for a breathing cycle will be a natural-number multiple of the switching cycle of the sound information HD for a heartbeat cycle. Accordingly, a switching timing for the sound information BD for a breathing cycle coincides with a switching timing for the sound information HD for a heartbeat cycle. Hence, the human subject E is able to more readily recognize his/her own biological cycles, and as a result it is expected that sleep and the like of the human subject E will improve.

Third Embodiment

In the audio signal generation device 20 according to the first embodiment described above, the switching cycle for switching the sound information BD for a breathing cycle and the switching cycle for switching the sound information HD for a heartbeat cycle are set independently of each other. In contrast, an audio signal generation device 20 according to a third embodiment differs from that of the first embodiment in that in the audio signal generation device 20 according to the third embodiment a switching cycle for switching sound information HD for a heartbeat cycle is set so as to be linked to a breathing cycle BRm of a human subject. Regarding other features, the audio signal generation device 20 according to the third embodiment is configured in substantially the same way as the audio signal generation device 20 according to the first embodiment.

Figure 8:
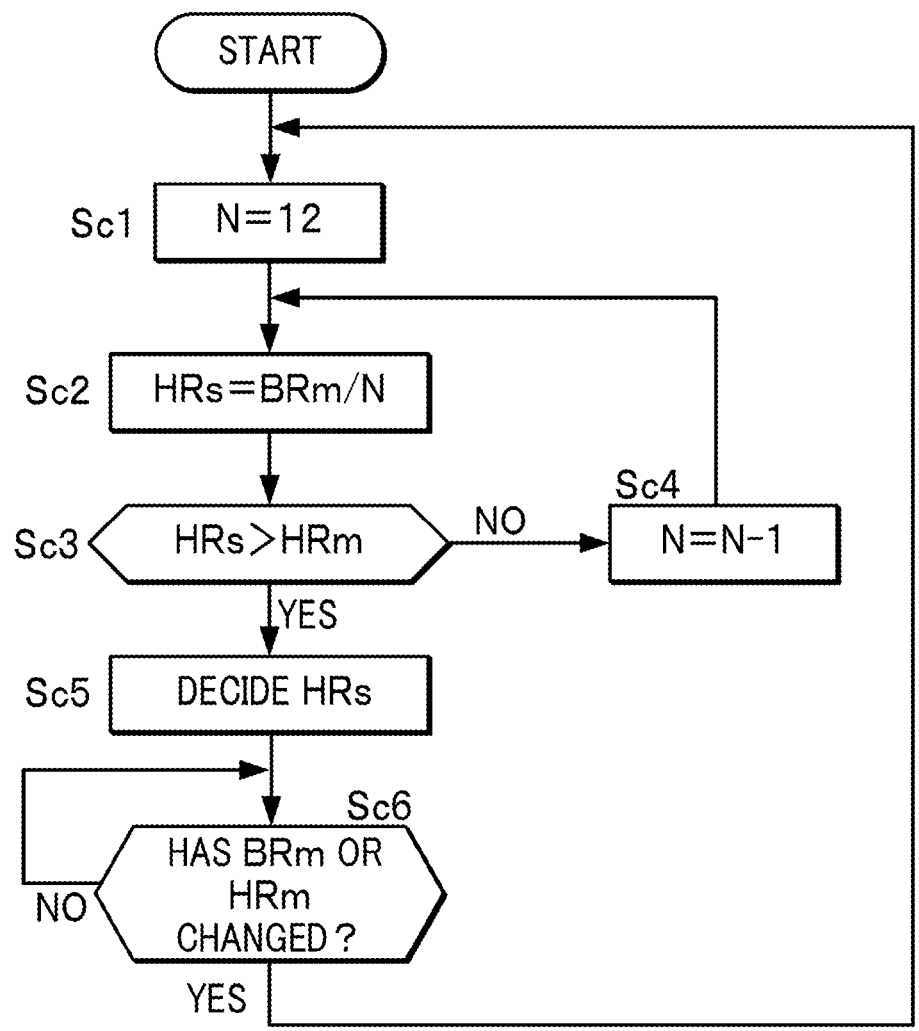
FIG. 8 is a flowchart showing a flow of an operation of a controller according to a third embodiment.

FIG. 8 is a flowchart showing a flow of an operation for deciding a switching cycle of sound information HD for a heartbeat cycle. First, a sound information manager 240 sets an initial value of a coefficient N to "12" (Sc1). Next, the sound information manager 240 calculates a switching cycle HRs in accordance with Expression 2 below (Sc2).

$$HRs = BRm/N \qquad \text{Expression 2}$$

Here, BRm is a breathing cycle measured by the biological cycle detector 215.

Next, the switching cycle decider 241 compares the calculated switching cycle HRs with the heartbeat cycle HRm measured by the biological cycle detector 215, and determines whether the switching cycle HRs extends beyond the heartbeat cycle HRm (Sc3). When the switching cycle HRs is equal to or less than the heartbeat cycle HRm, the switching cycle decider 241 advances the process to Sc4 and decrements the coefficient N by "1" (Sc4).

Then, the switching cycle decider 241 repeats each of the processes in steps Sc2 to Sc4 until the switching cycle HRs extends beyond the heartbeat cycle HRm. When the switching cycle HRs extends beyond the heartbeat cycle HRm, the switching cycle HRs is decided as a cycle at which the sound information pieces HD for a heartbeat cycle are switched (Sc5). For example, the measured breathing cycle BRm is 5.4 seconds and the measured heartbeat cycle HRm is 1 second. In the case of N=6, the switching cycle HRs is 0.9 seconds, and thus is less than the measured heartbeat cycle HRm, and so the switching cycle HRs is not decided as a cycle for switching the sound information pieces HD. In the case in which N becomes 5, however, the switching cycle HRs (1.08 seconds) extends beyond the measured heartbeat cycle HRm (1 second), and thus the switching cycle HRs will be 1.08 seconds.

Next, the switching cycle decider 241 determines whether either one of the measured breathing cycle BRm and the measured heartbeat cycle HRm has changed (Sc6). The sound information manager 240 repeats the determination until a determination condition is satisfied. When the determination condition is satisfied, the sound information manager 240 returns the process to step Sc1.

In the manner described above, the audio signal generation device 20 according to the third embodiment can switch sound information pieces HD for a heartbeat cycle, so as to be linked to the measured breathing cycle BRm. In the present example, the switching cycle HRs of the sound information HD for a heartbeat cycle is decided such that the switching cycle is one-Nth of the measured breathing cycle BRm (N is a natural number of 2 or more). However, the switching cycle of the sound information HD for a heartbeat cycle may be decided such that the switching cycle is one-Nth of the switching cycle BRs of the sound information pieces BD for a breathing cycle.

In this case, the switching cycle BRs of the sound information pieces BD for a breathing cycle is used in place of the measured breathing cycle BRm of the above description. The switching cycle HRs for a heartbeat cycle is one-Nth of the switching cycle BRs for a breathing cycle, and therefore, the switching cycle for a heartbeat cycle will be 1/natural-number of the switching cycle of the sound information BD for a breathing cycle. Accordingly, a switching timing for the sound information BD for a breathing cycle coincides with a switching timing for the sound information HD for a heartbeat cycle. Hence, the human subject E is able to more readily recognize his/her biological cycles, and as a result it is expected that sleep and the like of the human subject E will improve.

Fourth Embodiment

In the first to third embodiments described above, for each of the sound information BD for a breathing cycle, the sound information HD for a heartbeat cycle, and the sound information AD for an ambient sound, the audio signal generator 245 plays an audio signal based on a sound information piece D selected at random from the group designated by the setter 220, and as a result variations in audio signals are increased. For the purpose of improving sleep of the human subject E, the system 1 described above selects at random sound information pieces D so as to provide a wide variety of musical sounds to the human subject.

The audio signal generation device 20 of the embodiments described above is capable of concurrently outputting sounds of the sound information BD for a breathing cycle, the sound information HD for a heartbeat cycle, and the sound information AD for an ambient sound that is independent of biorhythms. The sound information pieces D to be played include sound information pieces D containing so-called musical intervals and chords. Thus, in cases where sound information pieces D selected at random are played at the same time, combinations of sounds will occur that are musically dissonant, and are likely to cause feelings of discomfort in the human subject E.

In this respect, an audio signal generation device 20 according to a fourth embodiment controls selection of waveform data pieces so that dissonance does not occur among a plurality of sound information pieces D, each of which serves as a base for output of sounds at the same time.

The audio signal generation device 20 according to the fourth embodiment is configured in substantially the same way as the audio signal generation device 20 according to the first embodiment, with the exception that sound information D includes attribute information indicative of a musical characteristic of the sound information D, and sound information pieces D are selected in accordance with a rule that defines combinations of musical characteristics that are allowed (or not allowed) to be output concurrently as sounds.

The attribute information may be in a freely selected form, provided that the information is indicative of a musical characteristic. The attribute information of the present embodiment includes a tonality (e.g., C major and A minor), a chord name (e.g., C7 and CM7), a note name (e.g., Do and Mi), a scale (e.g., a D Dorian scale and a C Okinawan scale), and a type of musical sound (e.g., a chordal structure and a modal structure). Chords are present in music that has a harmonic structure (chordal structure), while modes are present in music that relies on scales themselves and is not reliant on dominant motion (modal structure). The chordal structure includes musical characteristics, such as tonalities and chord names.

To avoid causing discomfort in a person, each of the notes output at the same time must have the same tonality in common in the chordal structure. Then, consideration is given to a chord name. For example, when sound information HD for a heartbeat cycle is CM7 (Do, Mi, Sol, Ti), and sound information for a breathing cycle is Dm7 (Re, Fa, La, Do), then dissonance may be perceived. Meanwhile, when the sound information HD for a heartbeat cycle is Am (La, Do, Mi) and the sound information BD for a breathing cycle is C6 (Do, Mi, Sol, La), then a person will not experience discomfort. That is, when note names constituting the chord name of one of the sound information pieces output concurrently as sounds include all note names constituting the chord name of the other sound information piece (i.e., when there is an inclusive relationship therebetween), the person will not experience discomfort even if the sound information pieces are concurrently output as sounds. On the contrary, where there is no inclusive relationship, as in the case of Dm7 (Re, Fa, La, Do) and CM7 (Do, Mi, Sol, Ti), the person will experience discomfort. As will be described later, when a musical characteristic of sound information D corresponds to a chordal structure, a sound information selector 242 selects, based on tonality and chord names, sound information pieces D to be output concurrently as sounds, so that the person does not experience discomfort.

The categorization according to modes is a method of categorizing music and is referred to as the church modes, and names of the modes such as C Dorian scale, E Lydian scale and so forth represent musical characteristics. Here, "C" in the C Dorian or "E" in the E Lydian refers to the tonic or keynote of the mode (i.e., a tonal center). Moreover, for a modal structure, a scale peculiar to a certain kind of ethnic music may be designated, instead of a scale of church modes. For example, such scales include the Okinawan scale, the Spanish scale, and the Gamelan scale (pelog scale). These scales may also be treated in substantially the same way as the church modes, when the tonic or keynote (tonal center) and a scale name thereof is designated. The modal structure has an extensible quality of being adaptable to cases where novel scales that do not exist at present are created in the future.

The sound information manager 240 extracts attribute information for each of the plurality of sound information pieces D stored in the storage unit 250, creates a control table TBLb, and stores the created control table TBLb in the storage unit 250. FIG. 9 shows an example of the control table TBLb.

Here, fields marked with "-" indicate null fields. For example, "BD1", "BD2", "HD3", and "HD4" are categorized into chordal structures, and each includes a chord name. In this case, a note name is null and a scale, which is peculiar to the modal structure, is also null. On the contrary, "HD1" and "HD2" are categorized into modal structures, and each includes a scale. In this case, a note name is null and a tonality and a chord name that are peculiar to a chordal structure, also are null. Next, referring to the sound information pieces "AD1" and "AD2" for an ambient sound, a note name is designated, but the remainder is null. Thus "AD1" is indicated as consisting solely of "Do" and the sound "Do" is output constantly; and "AD2" is indicated as consisting of two notes, "Do" and "Mi". For "AD3", all musical characteristics are null. This indicates a case in which sound information consists of nature sounds, such as a sound of waves and a murmuring sound of a stream.

Figure 10:
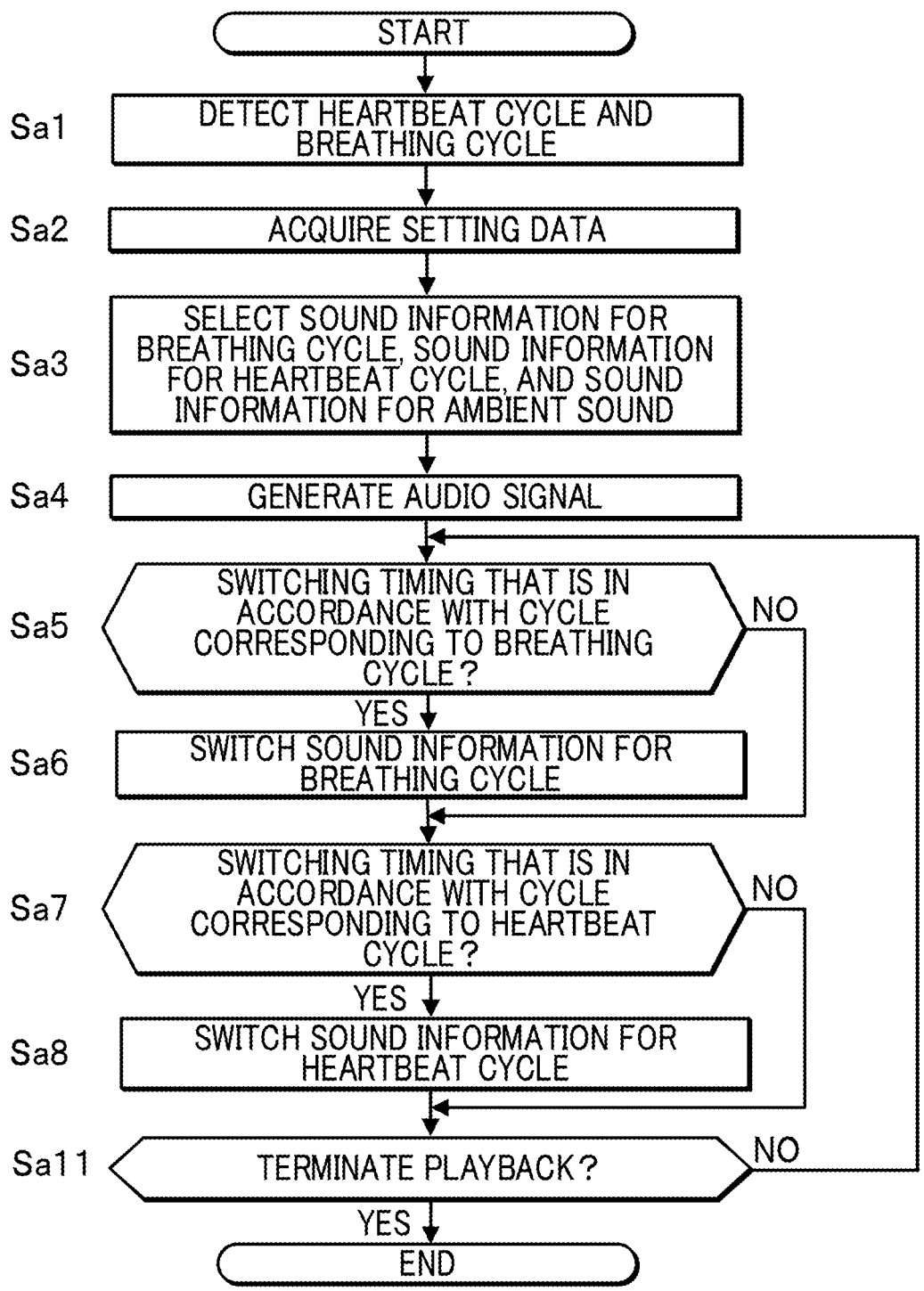
FIG. 10 is a flowchart showing a flow of an operation of the audio signal generation device also according to the fourth embodiment.

An operation of the audio signal generation device 20 of the fourth embodiment will now be explained. FIG. 10 is a flowchart showing a flow of an example of an operation according to the fourth embodiment. The operation of the audio signal generation device 20 of the fourth embodiment differs from that of the audio signal generation device 20 of the first embodiment, as shown in FIG. 6, in that the audio signal generation device 20 of the fourth embodiment does not switch the sound information AD for an ambient sound (steps Sa9 and Sa10 in FIG. 6). That is, when the determination condition in step Sa7 is denied, and when the process in step Sa8 is completed, the process proceeds to step Sa5.

In the first embodiment, sound information pieces D belonging to a prescribed group are switched by random selection. In addition to this, in the fourth embodiment the sound information selector 242 selects at random a sound information piece BD for a breathing cycle from sound information pieces BD belonging to a prescribed group and a sound information piece HD for a heartbeat cycle from sound information pieces HD belonging to a prescribed group, on condition that the selected sound information pieces conform to a concurrent sound output rule that defines combinations of musical characteristics that are allowed to be output concurrently as sounds.

More specifically, in step Sa3, the sound information selector 242 selects at random a sound information piece AD for an ambient sound from the group that has been set. In the present example, it is assumed that the sound information AD1 for an ambient sound shown in FIG. 9 is selected. Next, the sound information selector 242, with reference to the control table TBLb and in accordance with the concurrent sound output rule, selects a sound information piece BD for a breathing cycle and a sound information piece HD for a heartbeat cycle at random but such that the sound information pieces do not conflict with the note name "Do", which musically characterizes the sound information AD1 for an ambient sound.

Specifically, a sound information piece BD for a breathing cycle is selected at random from the sound information pieces BD for a breathing cycle that each include the note "Do" designated by the note name of the sound information AD for an ambient sound (concurrent sound output rule) and that belong to the designated group. The sound information HD for a heartbeat cycle is selected as follows.

(a1) First condition: the sound information HD for a heartbeat cycle must include a note designated by the note name of the sound information AD for an ambient sound (concurrent sound output rule).

When no note name is designated in the sound information AD for an ambient sound (e.g., sound of waves), the first condition is disregarded.

(a2) Second condition: the sound information HD for a heartbeat cycle must belong to the designated group.

(a3) Third condition: when the selected sound information BD for a breathing cycle has a modal structure, the sound information HD for a heartbeat cycle must have the same scale as that of the selected sound information BD for a breathing cycle (concurrent sound output rule).

(a4) Fourth condition: when the selected sound information BD for a breathing cycle has a chordal structure:
the tonality of the sound information HD for a heartbeat cycle must be the same as the tonality of the selected sound information BD for a breathing cycle; AND
the sound information HD for a heartbeat cycle must have a chord including all notes constituting the chord of the selected sound information BD for a breathing cycle (i.e., includes the notes constituting the chord of the sound information BD for a breathing cycle); or all notes constituting the chord of the sound information HD for a heartbeat cycle must be included in the notes constituting the chord of the selected sound information BD for a breathing cycle (i.e., the notes constituting the chord of the sound information HD for a heartbeat cycle are included in the notes constituting the chord of the sound information BD for a breathing cycle). (concurrent sound output rule) For example, it is assumed that the selected sound information BD for a breathing cycle is "BD2" shown in FIG. 9. In this case, since the chord of the sound information BD2 is CM7, the constituent notes thereof are "Do, Mi, Sol, and Ti". A chord including all notes constituting the chord of the sound information BD for a breathing cycle is CM7. Meanwhile, a chord, the constituent notes of which are entirely included in the notes constituting the chord of the sound information BD for a breathing cycle, is Em (Mi, Sol, Ti) and C (Do, Mi, Sol), for example. Accordingly, for sound information HD for a heartbeat cycle, one that includes a chord of CM7, Em, or C may be selected.

The tonality of the sound information BD2 for a breathing cycle is "C major", and therefore, for sound information HD for a heartbeat cycle, one that is in the tonality of "C major" may be selected. In other words, for sound information HD for a heartbeat cycle, one that is in the tonality of "C major" and has a chord of CM7, Em, or C, may be selected.

(a5) Fifth condition: the sound information HD for a heartbeat cycle must be selected randomly from sound information pieces HD for a heartbeat cycle satisfying the first, second, and third conditions, or from sound information pieces HD for a heartbeat cycle satisfying the first, second, and fourth conditions.

In the process of switching sound information BD for a breathing cycle in step Sa6 shown in FIG. 10, the sound information selector 242 switches the sound information pieces BD for a breathing cycle with reference to the control table TBLb and in accordance with the concurrent sound output rule.

In this case, the sound information BD for a breathing cycle is selected as follows.

(b1) First condition: the sound information BD for a breathing cycle must include a note designated by the note name of the sound information AD for an ambient sound (concurrent sound output rule).

When no note name is designated in the sound information AD for an ambient sound, the first condition is disregarded.

(b2) Second condition: the sound information BD for a breathing cycle must belong to the designated group.

(b3) Third condition: when the sound information HD for a heartbeat cycle being played has a modal structure, the sound information BD for a breathing cycle must have the same scale as that of the sound information HD for a heartbeat cycle (concurrent sound output rule).

(b4) Fourth condition: when the sound information HD for a heartbeat cycle being played has a chordal structure:
the tonality of the sound information BD for a breathing cycle must be the same as the tonality of the sound information HD for a heartbeat cycle being played; AND
the sound information BD for a breathing cycle must have a chord including all notes constituting the chord of the sound information HD for a heartbeat cycle; or the sound information BD for a breathing cycle must have a chord, the constituent notes of which are entirely included in the notes constituting the chord of the sound information HD for a heartbeat cycle. (concurrent sound output rule)

(b5) Fifth condition: the sound information BD for a breathing cycle must be selected randomly from sound information pieces BD for a breathing cycle satisfying the first, second, and third conditions, or from sound information pieces BD for a breathing cycle satisfying the first, second, and fourth conditions.

In the process of switching sound information HD for a heartbeat cycle in step Sa8 shown in FIG. 10, the sound information manager 240 switches the sound information pieces HD for a heartbeat cycle with reference to the control table TBLb and in accordance with the concurrent sound output rule.

In this case, the sound information HD for a heartbeat cycle is selected as follows (concurrent sound output rule).

(c1) First condition: the sound information HD for a heartbeat cycle must include a note designated by the note name of the sound information AD for an ambient sound.

When no note name is designated in the sound information AD for an ambient sound, the first condition is disregarded.

(c2) Second condition: the sound information HD for a heartbeat cycle must belong to the designated group.

(c3) Third condition: when the sound information BD for a breathing cycle being played has a modal structure, the sound information HD for a heartbeat cycle must have the same scale as that of the sound information BD for a breathing cycle (concurrent sound output rule).

(c4) Fourth condition: when the sound information BD for a breathing cycle being played has a chordal structure:
the tonality of the sound information HD for a heartbeat cycle must be the same as the tonality of the sound information BD for a breathing cycle being played; AND
the sound information HD for a heartbeat cycle must have a chord including all notes constituting the chord of the sound information BD for a breathing cycle; or the sound information HD for a heartbeat cycle must have a chord, the constituent notes of which are entirely included in the notes constituting the chord of the sound information BD for a breathing cycle. (concurrent sound output rule)

(c5) a condition: the sound information HD for a heartbeat cycle must be selected randomly from sound information pieces HD for a heartbeat cycle satisfying the first, second, and third conditions, or from sound information pieces HD for a heartbeat cycle satisfying the first, second, and fourth conditions.

Thus, in switching the sound information D of one of the sound information BD for a breathing cycle and the sound information HD for a heartbeat cycle, while the sound information D of the other one of the BD and HD is being played, the audio signal generator 245 of the present embodiment switches the sound information D such that a combination of the musical characteristic indicated by the attribute information of the sound information of one of the BD and HD and the musical characteristic indicated by the attribute information of the sound information of the other one of the BD and HD conform to the concurrent sound output rule.

Figure 11:
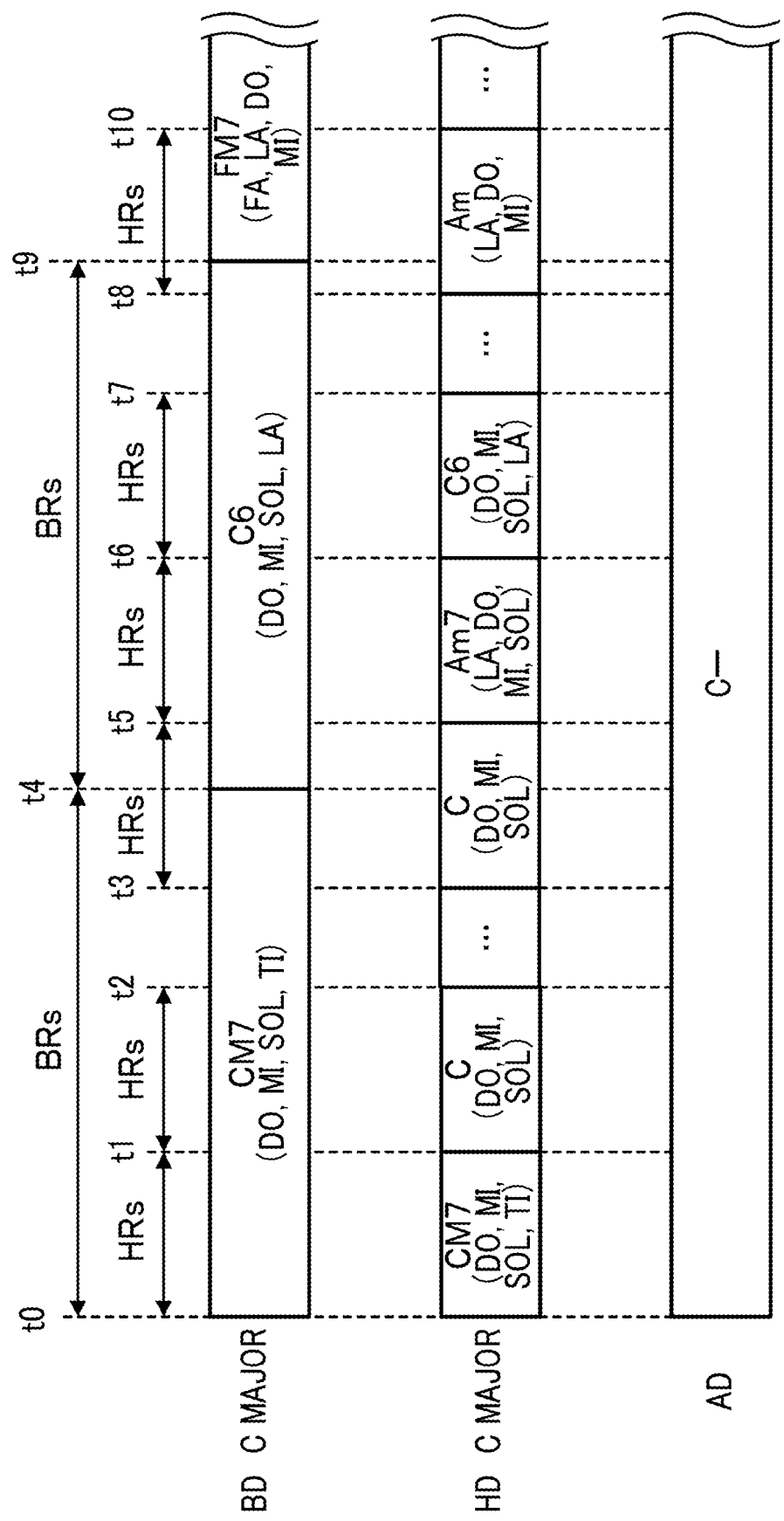
FIG. 11 is an explanatory diagram showing an example of switching of waveform data performed by the audio signal generation device again according to the fourth embodiment.

Next, description will be given of a concrete example of switching of sound information pieces BD for a breathing cycle and sound information pieces HD for a heartbeat cycle while taking musical characteristics into consideration. FIG. 11 is an explanatory diagram showing an example of switching of sound information pieces BD for a breathing cycle and switching of sound information pieces HD for a heartbeat cycle. In the present example, the tonalities of the sound information BD for a breathing cycle and the sound information HD for a heartbeat cycle are both C major. Moreover, the note of the sound information AD for an ambient sound is "Do", as shown in the figure.

Sound information pieces BD for a breathing cycle are switched from one to another at time points t4 and t9 shown in the figure, and sound information pieces HD for a heartbeat cycle are switched from one to another at time points t1, t2, t3, t5, t6, t7, t8, and t10 shown in the figure. Each "BRs" shown in the figure is indicative of the switching cycle for switching the sound information BD for a breathing cycle, and each "HRs" shown in the figure is indicative of the switching cycle for switching the sound information HD for a heartbeat cycle.

At the time point t1, for example, the switching timing for the sound information HD for a heartbeat cycle arrives while the sound information BD for a breathing cycle having a CM7 chord (Do, Mi, Sol, Ti) is being played. In the present example, a sound information piece HD for a heartbeat cycle is switched to a sound information piece HD for a heartbeat cycle having a C chord (Do, Mi, Sol). The notes "Do, Mi, and Sol" constituting the C chord are entirely included in the notes "Do, Mi, Sol, and Ti" constituting the CM7 chord, hence there is a match between the musical characteristics. Accordingly, a person does not experience discomfort when the sound information pieces HD for a heartbeat cycle are switched.

At the time point t4, the switching timing for the sound information BD for a breathing cycle arrives while the sound information HD for a heartbeat cycle having a C chord (Do, Mi, Sol) is being played. In the present example, a sound information piece BD for a breathing cycle is switched to a sound information piece BD for a breathing cycle having a C6 chord (Do, Mi, Sol, La). The notes "Do, Mi, and Sol" constituting the C chord are entirely included in the notes "Do, Mi, Sol, and La" constituting the C6 chord, hence there is a match between the musical characteristics. Accordingly, a person does not experience discomfort when the sound information pieces BD for a breathing cycle are switched.

In the present embodiment as described above, the sound information BD for a breathing cycle, the sound information HD for a heartbeat cycle, and the sound information AD for an ambient sound are selected in conformity with the concurrent sound output rule that defines combinations of musical characteristics that are allowed to be output concurrently as sounds, based on the musical characteristics indicated by the attribute information pieces with regard to the respective sound information pieces D. Thus, combination of sound information pieces that cause a person to experience discomfort can be suppressed. Further, according to the audio signal generation device 20 of the present embodiment, while increasing variations of sounds by switching various sound information pieces D between one another, the played sounds are perceived by a person as being natural. Thus, a quality of sleep can be enhanced by using the audio signal generation device 20.

In addition, in the present embodiment, attribute information is included in the sound information D, and a musical characteristic is determined based on the attribute information. Hence, even in cases where a new piece of sound information D is downloaded to the audio signal generation device 20 via the Internet, for example, the sound information D can be selected in accordance with the concurrent sound output rule. Consequently, the sound information D stored in the storage unit 250 has an extensible quality.

MODIFICATIONS

The present invention is not limited to the embodiments described above, and various applications and modifications thereof as described below are possible. Furthermore, one or a plurality of modes of the applications and modifications described below may be freely selected and combined, as appropriate.

Modification 1

In the foregoing embodiments, a sheet-like sensor 11 is used to detect biological information of the human subject E. However, the present invention is not limited thereto, and a freely selected sensor may instead be used in so far as the sensor is capable of detecting biological information. For example, an electrode of a first sensor may be attached to the forehead of a human subject E to detect brain waves (e.g., α waves, β waves, δ waves, and θ waves) of the human subject E. Moreover, a second sensor may be attached to a wrist of the human subject E to detect pressure changes in the radial artery, i.e., pulse waves. Since pulse waves are synchronous with heartbeats, heartbeats are also detected indirectly. Furthermore, a third sensor for detecting acceleration may be provided between the head of the human subject E and a pillow, to detect body motion (specifically, breathing, heartbeats, etc.) of the human subject E.

When an estimator 230 estimates a physical and mental state in a case in which a biological cycle detector 215 detects brain waves, a calm state in which there is relatively little body motion yet β waves are dominant in a brainwave pattern of the human subject E is estimated by the estimator 230 as an "awake" state. A state where θ waves are present in the brainwave pattern of the human subject E is estimated as a "light sleep" state. A state where δ waves are present in the brainwave pattern of the human subject E is estimated as a "deep sleep" state. A state where θ waves are present in the brainwave pattern of the human subject E yet breathing is shallow and irregular is estimated as a "REM-sleep" state. To carry out these estimations, a variety of approaches other than the above may also be used.

Modification 2

In the foregoing embodiments, a plurality of sound information pieces BD for a breathing cycle are managed by being grouped into a plurality of groups, a plurality of sound information pieces HD for a heartbeat cycle are managed by being grouped into a plurality of groups, and a plurality of sound information pieces AD for an ambient sound are managed by being grouped into a plurality of groups. Thus, the sound information selector 242 selects at random one sound information piece BD for a breathing cycle from some (i.e., a group) of a plurality of sound information pieces BD for a breathing cycle stored in the storage unit 250; then, at a cycle that is in accordance with a breathing cycle BRm, the audio signal generator 245 generates an audio signal V that is based on the selected sound information piece BD for a breathing cycle. The present invention is not limited thereto, and selection may be made from among the entirety of the sound information pieces BD for a breathing cycle stored in the storage unit 250. In the foregoing embodiments, the sound information selector 242 also selects at random one sound information piece HD for a heartbeat cycle from among some (i.e., a group) of a plurality of sound information pieces HD for a heartbeat cycle stored in the storage unit 250; then, at a cycle that is in accordance with a heartbeat cycle HRm, the audio signal generator 245 generates an audio signal V that is based on the selected sound information piece HD for a heartbeat cycle. The present invention is not limited thereto, and selection may be made from among the entirety of the sound information pieces HD for a heartbeat cycle stored in the storage unit 250. Moreover, a group from which a sound information piece D is selected may be changed, as appropriate, in accordance with a prescribed rule.

Modification 3

In the first to third embodiments described above, a sound information piece AD for an ambient sound is switched to a new sound information piece AD at a prescribed cycle; however, the present invention is not limited thereto, and as in the fourth embodiment, the sound information AD may not be switched. Moreover, in the fourth embodiment, sound information AD for an ambient sound is not switched, but the present invention is not limited thereto; when a prescribed cycle has elapsed or a prescribed condition is satisfied, a sound information piece AD for an ambient sound may be switched to a new sound information piece AD.

Modification 4

In the embodiments described above, the history information generator 244 associates a physical and mental state estimated by the estimator 230 and an identifier of a selected sound information piece D with a processing time of the selected sound information piece D, and stores the same in the history table TBLa. Thus, by referring to the history table TBLa, it is possible to identify a sound information piece that is preferable for the human subject E; for example, to identify a sound information piece, the use of which causes a period extending from going to bed to sleep onset to be made shorter. In this case, a combination of a group of sound information pieces BD for a breathing cycle, a group of sound information pieces HD for a heartbeat cycle, and a group of sound information pieces AD for an ambient sound may be identified based on identifiers of sound information pieces in the history table TBLa. Specifically, it is possible to identify which combination of groups is suitable for a transitional course from "awake" to "light sleep", or to identify which combination of groups is suitable for a transitional course from "light sleep" to "deep sleep", for example.

By referring to the history table TBLa, a sound information selector 242 may automatically switch, in accordance with an estimated physical and mental state, at least one of a group from which sound information BD for a breathing cycle is selected, a group from which sound information HD for a heartbeat cycle is selected, and a group from which sound information AD for an ambient sound is selected.

Furthermore, in a case in which the human subject E does not fall asleep easily, i.e., in a case in which a prescribed condition is satisfied, such as a period extending from going to bed to sleep onset being longer than an average period of the human subject E, by referring to the history table TBLa the sound information selector 242 may automatically switch to a group by use of which it is highly probable that the human subject E will be able to fall asleep quickly. As described above, by evaluating a sleep state (specifically, an estimated physical and mental state) of the human subject E and feeding back the same for selection of sound information D, a quality of sleep can be enhanced to a great extent.

Modification 5

In the fourth embodiment described above, attribute information is used to determine a musical characteristic of each sound information piece; combinations of sound information pieces that are allowed, or not allowed, to be output concurrently as sounds are identified based on the musical characteristics; and the identified combinations are reflected on selection of sound information pieces D. The present invention is not limited thereto, and a freely-selected method may be used as far as a concurrent sound output rule can be realized. For example, attribute information and/or a control table TBLb need not be used. Specifically, a table may be prepared in advance in which data names of sound information pieces D and data names for which concurrent sound output is allowed are associated with each other, and sound information D may be selected by referring to this table. In this case, the sound information selector 242 selects each of sound information BD for a breathing cycle and sound information HD for a heartbeat cycle in accordance with a concurrent sound output rule that defines combinations of musical characteristics that are allowed to be concurrently output as sounds.

In the fourth embodiment described above, a tonality was fixed for a chordal structure; however, the present invention is not limited thereto. For example, an FM7 chord belongs to C major and F major, as shown in FIG. 9. A case is assumed where, in switching sound information pieces BD for a breathing cycle and sound information pieces HD for a heartbeat cycle in C major, "BD3" shown in FIG. 9 is selected for sound information BD for a breathing cycle and "HD5" shown in the figure is selected for sound information HD for a heartbeat cycle. In this case, sound information BD for a breathing cycle or sound information HD for a heartbeat cycle to be selected next may be either in C major or F major.

In the fourth embodiment described above, a tonality and a chord name are both taken into consideration for a concurrent sound output rule; however, the present invention is not limited thereto. For example, concurrent sound output may be allowed, provided that a tonality is identical. Moreover, whether to employ a tonality alone as a condition for allowing concurrent sound output, or to employ both a tonality and a chord name as conditions for allowing concurrent sound output, may be selected automatically, or may be input by a person using an input device 225.

Modification 6

In the embodiments described above, the audio signal generator 245 acquires sound information D from the storage unit 250; however, the present invention is not limited thereto, and the sound information D may be stored anywhere in so far as the sound information D can be acquired. For example, the audio signal generation device 20 may include a communicator capable of communicating with a server connected to a communication network, and the audio signal generation device 20 may acquire the sound information D stored in the server, via the communicator. In this case, the server may be provided in the same facility, or may be provided remotely. That is, the audio signal generator 245 may acquire the sound information D via a communication network, such as the Internet.

The following configurations may be envisaged from the embodiments described above. That is, in one aspect, an audio signal generation device according to the present invention includes: an acquirer configured to acquire biological information of a human subject; an audio signal generator configured to generate an audio signal based on at least one of a plurality of pieces of sound information; and a switching cycle decider configured to decide a switching cycle, such that first sound information switches to second sound information at a cycle that is in accordance with the biological information, the first sound information and the second sound information being included in the plurality of sound information pieces, and the audio signal generator generates an audio signal based on the second sound information at the switching cycle decided by the switching cycle decider.

According to this aspect, an audio signal is generated by switching from the first sound information to the second sound information at a cycle that is in accordance with the biological information. Thus, unlike loop playback in which the same sound information is used repeatedly, in this mode there can be produced a greater variety in sounds to be played. Moreover, a switching cycle at which a sound information piece is switched to a new sound information piece (second sound information) can be set to a cycle that is in accordance with the biological information, and therefore, sleep and the like of the human subject can be enhanced. Here, the cycle that is in accordance with the biological information need not necessarily coincide with a biological cycle of the human subject (for example, a breathing cycle or a heartbeat cycle) that is obtained from the biological information, but may be a cycle that is obtained based on a particular relationship with the biological information.

In the audio signal generation device described above, in a preferred mode, the second sound information is selected at random from among the plurality of sound information pieces. In this mode, since sound information is selected at random, sound information provided to the human subject is made unpredictable, as a result of which neither boredom nor annoyance is caused to arise in the human subject. Storage of a large amount of sound information to enable provision of a wide variety of sounds to prevent boredom or annoyance arising in the human subject requires use of a large-capacity storage unit. In the above preferred mode, however, since sound information is switched at random for generation of an audio signal that causes neither boredom nor annoyance in the human subject, there can be used a relatively small-capacity storage unit. Inherent to sounds that have a relaxing or healing effect are natural fluctuation components. By randomly playing such sounds, differing fluctuation components can be imparted to the entirety of the played sounds. It is of note here that the concept of randomness includes so-called pseudo randomness.

In a preferred mode of the audio signal generation device the plurality of sound information pieces include a plurality of sound information pieces for a breathing cycle and a plurality of sound information pieces for a heartbeat cycle, the audio signal generator generates the audio signal by generating an audio signal for a breathing cycle based on one of the plurality of sound information pieces for a breathing cycle, generating an audio signal for a heartbeat cycle based on one of the plurality of sound information pieces for a heartbeat cycle, and synthesizing the audio signal for a breathing cycle and the audio signal for a heartbeat cycle, the switching cycle decider decides a switching cycle for a breathing cycle in accordance with a breathing cycle of the human subject obtained based on the biological information, wherein the switching cycle for a breathing cycle is the switching cycle of the plurality of sound information pieces for a breathing cycle, and decides a switching cycle for a heartbeat cycle in accordance with a heartbeat cycle of the human subject obtained based on the biological information, wherein the switching cycle for a heartbeat cycle is the switching cycle of the plurality of sound information pieces for a heartbeat cycle, and the sound information selector selects at random one of the plurality of sound information pieces for a breathing cycle as the second sound information, and selects at random one of the plurality of sound information pieces for a heartbeat cycle as the second sound information.

In this mode, the sound information pieces for a breathing cycle are switched at random, as are the sound information pieces for a heartbeat cycle, and therefore, variations of sounds to be played based on the audio signals can be further increased. Moreover, since the switching cycle accords with either the breathing cycle or the heartbeat cycle of the human subject, an audio signal that is linked to a physical and mental state of the human subject can be generated, resulting in further enhancement in sleep and the like.

Random selection of one of a plurality of sound information pieces for a breathing cycle involves selection from among some of the plurality of sound information pieces for a breathing cycle, or selection from among all of the plurality of sound information pieces for a breathing cycle. Likewise, random selection of one of a plurality of sound information pieces for a heartbeat cycle involves selection from among some of the plurality of sound information pieces for a heartbeat cycle, or selection from among all of the plurality of sound information pieces for a heartbeat cycle.

In the audio signal generation device described above, in a preferred mode, the switching cycle decider decides the switching cycle for a heartbeat cycle either in accordance with a cycle that is one-Nth of the breathing cycle, where N is a natural number of 2 or more, or in accordance with a cycle that is one-Nth of the switching cycle for a breathing cycle, rather than deciding the switching cycle for a heartbeat cycle in accordance with the heartbeat cycle. In this mode, the switching cycle of the sound information pieces for a heartbeat cycle can be either one-Nth of the breathing cycle of the human subject or one-Nth of the switching cycle of the sound information pieces for a breathing cycle. Accordingly, in a case that a first period is a period that commences from a start of generation of an audio signal based on a sound information piece (first sound information) for a breathing cycle and extends up to a time point of switching to a new sound information piece (second sound information) for a breathing cycle, and a second period is a period that commences from a start of generation of an audio signal based on a sound information piece (first sound information) for a heartbeat cycle and extends up to a time point of switching to a new sound information piece (second sound information), a period corresponding to an N-number multiple of the second period is the same as the first period. Consequently, an audio signal that is generated based on sound information for a breathing cycle, and an audio signal that is generated based on sound information for a heartbeat cycle are interlinked, and as a result the human subject perceives a natural sound.

In the audio signal generation device described above, in a preferred mode, the switching cycle decider decides the switching cycle for a breathing cycle either in accordance with a cycle that is an N-number multiple of the heartbeat cycle, where N is a natural number of 2 or more, or in accordance with a cycle that is an N-number multiple of the switching cycle for a heartbeat cycle, rather than deciding the switching cycle for a breathing cycle in accordance with the breathing cycle. In this mode, the switching cycle of the sound information for a breathing cycle can be an N-number multiple of the switching cycle of the sound information pieces for a heartbeat cycle. Accordingly, in a case that a first period is a period that commences from a start of generation of an audio signal based on a sound information piece (first sound information) for a breathing cycle and extends up to a time point of switching to a new sound information piece (second sound information) for a breathing cycle, and a second period is a period that commences from a start of generation of a sound information piece (first sound information) for a heartbeat cycle and extends up to a time point of switching to a new sound information piece (second sound information), a period corresponding to an N-number multiple of the second period is the same as the first period. Consequently, an audio signal that is generated based on sound information for a breathing cycle and an audio signal that is generated based on sound information for a heartbeat cycle are interlinked, and as a result the human subject perceives a natural sound.

In the audio signal generation device described above, in a preferred mode, the sound information selector selects sound information pieces for a breathing cycle and sound information pieces for a heartbeat cycle in accordance with a sound output rule that defines a combination of musical characteristics each of which can be output concurrently as sounds. In this mode, concurrent sound output is controlled in accordance with a concurrent sound output rule that defines combinations of musical characteristics that may be concurrently output as sounds. As a result, there can be avoided output at the same time of a sound corresponding to a sound information piece for a breathing cycle and a sound corresponding to a sound information piece for a heartbeat cycle, where the respective sounds are not musically harmonious. Consequently, perception by the human subject of sounds that are not musically harmonious is minimized, and sleep and the like of the human subject can be enhanced.

In the audio signal generation device described above, in a preferred mode, each of the plurality of sound information pieces includes attribute information indicating a musical characteristic, and in a case in which the sound information for a heartbeat cycle is switched from the first sound information to the second sound information while the audio signal generator is generating the audio signal for a breathing cycle, the sound information selector selects sound information for a heartbeat cycle as the second sound information, such that a combination of a musical characteristic indicated by attribute information included in one of the sound information pieces for a breathing cycle that corresponds to the audio signal for a breathing cycle, which is being generated, and a musical characteristic indicated by attribute information included in the sound information for a heartbeat cycle, which is the second sound information, conforms to the concurrent sound output rule, and in a case in which the sound information for a breathing cycle is switched from the first sound information to the second sound information while the audio signal generator is generating the audio signal for a heartbeat cycle, the sound information selector selects the sound information for a breathing cycle as the second sound information, such that a combination of a musical characteristic indicated by attribute information included in one of the sound information pieces for a heartbeat cycle that corresponds to the audio signal for a heartbeat cycle, which is being generated, and a musical characteristic indicated by attribute information included in the sound information for a breathing cycle, which is the second sound information, conforms to the concurrent sound output rule. In this mode, the second sound information for a breathing cycle is selected such that the following musical characteristics conform to the concurrent sound output rule:
a musical characteristic of the sound information piece for a breathing cycle corresponding to the audio signal for a heartbeat cycle that is being generated when the sound information for a breathing cycle is switched from the first sound information to the second sound information; and
a musical characteristic of the second sound information for a breathing cycle after the switch.

Likewise, the second sound information for a heartbeat cycle is selected such that the following musical characteristics conform to the concurrent sound output rule:
a musical characteristic of the sound information piece for a heartbeat cycle corresponding to the audio signal for a breathing cycle that is being generated when the sound information for a heartbeat cycle is switched from the first sound information to the second sound information; and
a musical characteristic of the second sound information for a heartbeat cycle after the switch.

Consequently, a possibility of the synthesized sound signal being discordant and annoying can be reduced.

The concurrent sound output rule may preferably be determined based on at least one of a tonality, a chord name, a type (chordal structure or modal structure), and a scale.

In the audio signal generation device described above, in a preferred mode, a maximum value of an amplitude of a waveform in a latter half period of a time length of the waveform is equal to or less than 50% of a maximum value of the amplitude of the waveform over the entire period of the time length of the waveform, the waveform being generated by the audio signal generator based on one of the plurality of sound information pieces. In a case in which the amplitude changes only slightly over the entire period of the time length of the waveform, then even if the first sound information is switched to the second sound information at a cycle that is in accordance with the biological information, it is only with difficulty that the human subject may distinctly perceive the cycle that is in accordance with the biological information. In contrast, in the preferred mode described above, in each of data pieces of the waveforms representing the respective sound information pieces, the maximum value of the amplitude in the latter half of the waveform is equal to or less than 50% of the maximum value of the amplitude of the entire waveform. Thus, the human subject can with relative ease perceive the cycle that is in accordance with the biological information. As a result, sleep also can be induced in the human subject with relative ease.

In a preferred mode of the present invention, the audio signal generation device further includes: an estimator configured to estimate a physical and mental state of the human subject; and a storage unit configured to store history information in which the physical and mental state estimated by the estimator and a sound information piece that was selected when the physical and mental state was estimated are associated with each other, and the plurality of sound information pieces are grouped into a plurality of groups, and with reference to the history information the sound information selector selects one of the groups in accordance with the physical and mental state estimated by the estimator, and selects as the second sound information one piece of sound information from the selected group. In the configuration described above, selection of a group from which the second sound information is selected is made from a plurality of groups. The selection of the group is made in accordance with history information and the physical and mental state that is estimated by the estimator, the history information consisting of physical and mental states and sound information stored together in association with each other. Thus, by feeding back the estimated physical and mental state for the selection of sound information, a quality of sleep can be greatly improved.

It is of note that the present invention may be embodied not only in a form of an audio signal generation device, but also in a form of an operation method for the audio signal generation device (i.e., an audio signal generation method); or in a form of a program that causes a computer to execute the audio signal generation method. By use of the information provision method and the program, substantially the same effects can be attained as those attained by the audio signal generation device. The program of the present invention may be stored on computer-readable storage media for installation in a computer.

DESCRIPTION OF REFERENCE SIGNS

1: system
11: sensor
20: audio signal generation device
51, 52: speakers
200: controller
210: acquirer
220: setter
225: input device
230: estimator
240: sound information manager
241: switching cycle decider 242: sound information selector
243: switching timing determiner
244: history information generator
245: audio signal generator
250: storage unit
TBLa: history table
TBLb: control table

The invention claimed is:
1. An audio signal generation device comprising:
at least one memory storing instructions; and
a controller including a processor that implements the instructions to execute a plurality of tasks, including:
an acquiring task that acquires biological information including a breathing cycle and a heartbeat cycle of a human subject;
an audio signal generating task that generates an audio signal based on;
a first plurality of sound information, including first sound information and second sound information, to be played at a first cycle associated with the breathing cycle; and
a second plurality of sound information, including third sound information and fourth sound information, to be played at a second cycle associated with the heartbeat cycle;
a sound information selecting task that selects the second sound information and the fourth sound information after the first sound information and the third sound information have been selected, wherein:
the second sound information specifies a first sound information piece to be played at the first cycle, from among a first plurality of sound information pieces to be played at the first cycle; and
the fourth sound information specifies a second sound information piece to be played at the second cycle, from among a second plurality of sound information pieces to be played at the second cycle; and
a switching cycle deciding task that decides, in accordance with the acquired biological information, for respectively switching the first sound information and the third sound information:
a first switching cycle for switching the first cycle; and
a second switching cycle for switching the second cycle,
wherein the audio signal generating task, based on the selected second sound information and the selected fourth sound information:
generates a first audio signal to be played at the first cycle based on the first sound information piece at the decided first switching cycle;
generates a second audio signal to be played at the second cycle based on the second sound information piece at the decided second switching cycle; and
synthesizes the audio signal from the generated first audio signal and the generated second audio signal.

2. The audio signal generation device according to claim 1, wherein the switching cycle deciding task decides the second switching cycle in accordance with the second cycle that is one-Nth, where N is a natural number of at least 2, of either the first cycle or the first switching cycle.

3. The audio signal generation device according to claim 2, wherein each of the first and second audio signals includes a waveform where a first maximum value of an amplitude of the waveform in a latter half period of a time length of the waveform is equal to or less than 50% of a second maximum value of the amplitude of the waveform over the time length of the waveform.

4. The audio signal generation device according to claim 1, wherein the switching cycle deciding task decides the first switching cycle in accordance with the first cycle that is an N-number multiple, where N is a natural number of at least 2, of either the second cycle or the second switching cycle.

5. The audio signal generation device according to claim 1, wherein the sound information selecting task selects one of the first plurality of sound information and one of the second plurality of sound information in accordance with a concurrent sound output rule that defines a combination of musical characteristics that are allowed to be output concurrently as sounds.

6. The sound information generation device according to claim 5, wherein:
each of the first and second plurality of sound information pieces includes attribute information indicating a musical characteristic,
the third sound information is switched to the fourth sound information while the first audio signal is being generated,
the sound information selecting task selects the fourth sound information, such that permits a first combination of a first musical characteristic indicated by first attribute information included in the first sound information piece and a second musical characteristic indicated by second attribute information included in the second sound information piece to conform with the concurrent sound output rule, and
the first sound information is switched to the second sound information while the second audio signal is being generated,
the sound information selecting task selects the second sound information that permits a second combination of a third musical characteristic indicated by third attribute information included in the second sound information piece and a fourth musical characteristic indicated by fourth attribute information included in the first sound information piece to conform with the concurrent sound output rule.

7. The audio signal generation device according to claim 1, wherein each of the first and second audio signals includes a waveform where a first maximum value of an amplitude of the waveform in a latter half period of a time length of the waveform is equal to or less than 50% of a second maximum value of the amplitude of the waveform over the time length of the waveform.

8. The audio signal generation device according to claim 1, wherein the plurality of tasks include:
an estimating task that estimates a physical and mental state of the human subject, based on the biological information; and
a storing task that stores, in the at least one memory, history information at associates the estimated physical and mental state and the selected sound information,
wherein the first plurality of sound information pieces are grouped into a first plurality of groups and the second plurality of sound information pieces are grouped into a second plurality of groups, and
wherein, the sound information selecting task selects the second sound information and the fourth sound information with reference to the history information.

9. An audio signal generation method of generating an audio signal, the method comprising:

acquiring biological information including a breathing cycle and a heartbeat cycle of a human subject;

generating an audio signal based on a first plurality of sound information, including first sound information and second sound information, to be played at a first cycle associated with the breathing cycle and a second plurality of sound information, including third sound information and fourth sound information, to be played at a second cycle associated with the heartbeat cycle;

selecting the second sound information and the fourth sound information after the first sound information and the third sound information have been selected, wherein:

the second sound information specifies a first sound information piece to be played at the first cycle, from among a first plurality of sound information pieces to be played at the first cycle; and the fourth sound information specifies a second sound information piece to be played at the second cycle, from among a second plurality of sound information pieces to be played at the second cycle; and deciding a switching cycle, in accordance with the acquired biological information, for respectively switching the first sound information and the third sound information:

a first switching cycle for switching the first cycle; and
a second switching cycle for switching the second cycle, wherein the generating of the audio signal:

generates a first audio signal to be played at the first cycle based on the first sound information piece at the decided first switching cycle;

generates a second audio signal to be played at the second cycle based on the second sound information piece at the decided second switching cycle; and synthesizes the audio signal from the generated first audio signal and the generated second audio signal.

10. The audio signal generation method according to claim 9, wherein the deciding of the switching cycle decides the second switching cycle in accordance with the second cycle that is one-Nth, where N is a natural number of at least 2, of either the first cycle or the first switching cycle.

11. The audio signal generation method according to claim 9, wherein the deciding of the switching cycle decides the first switching cycle in accordance with the second cycle that is an N-number multiple, where N is a natural number of at least two, of either the first cycle or the second switching cycle.

12. The audio signal generation method according to claim 9, wherein the selecting of the second sound information and the fourth sound information selects one of the first plurality of sound information and one of the second plurality of sound information in accordance with a concurrent sound output rule that defines a combination of musical characteristics that are allowed to be output concurrently as sounds.

13. The audio signal generation method according to claim 12, wherein:

each of the first and second plurality of sound information pieces includes attribute information indicating a musical characteristic, the third sound information is switched to the fourth sound information while the first audio signal is being generated, the selecting selects the fourth sound information that permits a first combination of a first musical characteristic indicated by first attribute information included in the first sound information piece and a second musical characteristic indicated by second attribute information included in the second sound information piece to conform with the concurrent sound output rule, and the first sound information is switched to the second sound information while the second audio signal is being generated, the selecting selects the second sound information that permits a second combination of a third musical characteristic indicated by third attribute information included in the second sound information piece and a fourth musical characteristic indicated by fourth attribute information included in the first sound information piece to conform with the concurrent sound output rule.

14. A non-transitory computer-readable storage medium storing therein a program executable by a computer to execute a method of generating an audio signal, the method comprising:

acquiring biological information including a breathing cycle and a heartbeat cycle of a human subject;

generating an audio signal based on a first plurality of sound information, including first sound information and second sound information, to be played at a first cycle associated with the breathing cycle and a second plurality of sound information, including third sound information and fourth sound information, to be played at a second cycle associated with the heartbeat cycle;

selecting the second sound information and the fourth sound information after the first sound information and the third sound information have been selected, wherein:

the second sound information specifies a first sound information piece to be played at the first cycle, from among a first plurality of sound information pieces to be played at the first cycle; and the fourth sound information specifies a second sound information piece to be played at the second cycle, from among a second plurality of sound information pieces to be played at the second cycle; and deciding a switching cycle, in accordance with the acquired biological information, for respectively switching the first sound information and the third sound information:

a first switching cycle for switching the first cycle; and
a second switching cycle for switching the second cycle, wherein the generating of the audio signal:

generates a first audio signal to be played at the first cycle based on the selected first sound information piece at the decided first switching cycle;

generates a second audio signal to be played at the second cycle based on the second sound information piece at the decided second switching cycle; and synthesizes the audio signal from the generated first audio signal and the generated second audio signal.

* * * * *